US012606797B2

(12) United States Patent
Slepian et al.

(10) Patent No.: US 12,606,797 B2
(45) Date of Patent: Apr. 21, 2026

(54) METHODS OF DETECTION OF MECHANICALLY-ACTIVATED PLATELET ACTIVATION AND USES THEREOF

(71) Applicants: Arizona Board of Regents on Behalf of the University of Arizona, Tucson, AZ (US); The Research Foundation for the State University of New York, Albany, NY (US)

(72) Inventors: Marvin J. Slepian, Tucson, AZ (US); Yana Roka-Moiia, Tucson, AZ (US); Danny Bluestein, Stony Brook, NY (US)

(73) Assignees: Arizona Board of Regents on Behalf of the University of Arizona, Tucson, AZ (US); The Research Foundation for The State University of New York, Albany, NY (US)

( * ) Notice: Subject to any disclaimer, the term of this patent is extended or adjusted under 35 U.S.C. 154(b) by 1096 days.

(21) Appl. No.: 17/252,577

(22) PCT Filed: Jun. 17, 2019

(86) PCT No.: PCT/US2019/037528
§ 371 (c)(1),
(2) Date: Dec. 15, 2020

(87) PCT Pub. No.: WO2019/241793
PCT Pub. Date: Dec. 19, 2019

(65) Prior Publication Data
US 2021/0277357 A1 Sep. 9, 2021

Related U.S. Application Data

(60) Provisional application No. 62/685,703, filed on Jun. 15, 2018.

(51) Int. Cl.
| | |
|---|---|
| *C12N 5/078* | (2010.01) |
| *A61K 35/19* | (2015.01) |
| *C12N 13/00* | (2006.01) |
| *G01N 33/68* | (2006.01) |

(52) U.S. Cl.
CPC ............ *C12N 5/0644* (2013.01); *A61K 35/19* (2013.01); *C12N 13/00* (2013.01); *G01N 33/68* (2013.01)

(58) Field of Classification Search
CPC ...... C12N 5/0644; C12N 13/00; A61K 35/19; G01N 33/68
See application file for complete search history.

(56) References Cited

U.S. PATENT DOCUMENTS

| | | | |
|---|---|---|---|
| 10,478,404 B2 * | 11/2019 | Slepian | ................. A61K 31/337 |
| 2005/0014770 A1 * | 1/2005 | Eisert | ..................... A61K 45/06 |
| | | | 514/262.1 |
| 2008/0153876 A1 * | 6/2008 | Sinha | ................... A61K 31/435 |
| | | | 514/343 |
| 2015/0056604 A1 * | 2/2015 | Sehgal | ................. A01N 1/0226 |
| | | | 435/2 |
| 2017/0246632 A1 | 8/2017 | Slepian | |
| 2018/0142199 A1 * | 5/2018 | Jones | ..................... C12M 21/08 |

FOREIGN PATENT DOCUMENTS

WO 2015113001 7/2015

OTHER PUBLICATIONS

Dimasi A, Roka-Moiia Y, Consolo F, Rasponi M, Fiore GB, Slepian MJ, Redaelli A. Microfluidic flow-based platforms for induction and analysis of dynamic shear-mediated platelet activation—Initial validation versus the standardized hemodynamic shearing device. Biomicrofluidics. May 22, 2018;12(4):042208 (Year: 2018).*

Dimasi et al. (Biomicrofluidics 12, 042208 (2018); published online May 22, 2018; referenced in IDS Cite No. 12 submitted Jan. 3, 2022 (Year: 2018).*

Marvin J. Slepian (UIUC Cell Mechanobiology 2015, titled Shear-Mediated Platelet Activation—Mechanotransduction in the Free Flow: A Vital Mechanism in Thrombosis of Cardiovascular Therapeutic Implant Systems., Published online https://mediaspace.illinois.edu/media/t/1_fwmr2g60/46797541, Mar. 29, 2016 (Year: 2016).*

Duvernay et al. (Biochemistry. Sep. 15, 2015; 54(36): 5578-5588. Published online Sep. 1, 2015. doi: 10.1021/acs.biochem.5b00549. (Year: 2015).*

Yin et al. (American Journal of Clinical Pathology, vol. 129, Issue 6, Jun. 2008, pp. 862-869. Jan. 6, 2008) (Year: 2008).*

Slepian (UIUC Cell Mechanobiology 2015, titled Shear-Mediated Platelet Activation—Mechanotransduction in the Free Flow: A Vital Mechanism in Thrombosis of Cardiovascular Therapeutic Implant Systems., Published online https://mediaspace.illinois.edu/media/t/1_fwmr2g60/46797541, Mar. 29, 2016 (Year: 2016).*

(Continued)

*Primary Examiner* — Fereydoun G Sajjadi
*Assistant Examiner* — Joel D Levin
(74) *Attorney, Agent, or Firm* — Pabst Patent Group LLP

(57) ABSTRACT

Biochemical markers that can be measured to determine the level of mechanical activation of a population of platelets are provided, and their use to prepare molecular signatures thereof are provided. The markers include phosphatidylserine, thrombin, integrin GPIIb/IIIa activation, glycoprotein GP Ib, P-selectin; platelet size; microparticle generation, or lipidomic profile of the membrane. The disclosed markers, measurement thereof, and signatures composed therefrom can be used in a variety of methods of patient selection, treatment monitoring, treatment selection, including both devices and active agents, and methods of treating subjects in need thereof, particularly humans. Examples of such methods include, but are not limited to, reducing shear-activated platelets; selecting a blood-contacting medical device; selecting between two or more medical devices; identifying a subject at a risk of developing a thrombogenic event; monitoring the prophylactic treatment of a subject; selecting a mechanoceutical agent; and delivering an agent to a subject.

20 Claims, 16 Drawing Sheets

(56)                    References Cited

OTHER PUBLICATIONS

Duvernay et al. (Biochemistry. Sep. 15, 2015; 54(36): 5578-5588. Published online Sep. 1, 2015. doi: 10.1021/acs.biochem.5b00549. (Year: 2016).*

Slatter et al. (Cell Metab. May 10, 2016;23(5):930-44. doi: 10.1016/j.cmet.2016.04.001. Epub Apr. 28, 2016. (Year: 2016).*

Rahman et al. (Acta Biomater. Jun. 2018:73:228-235. doi: 10.1016/j.actbio.2018.04.002. Epub Apr. 11, 2018. (Year: 2018).*

Slepian et al. (J Biomech. Jan. 4, 2017:50:20-25. doi: 10.1016/j.jbiomech.2016.11.016. Epub Nov. 10, 2016.) (Year: 2016).*

Alonso, "Arachidonic acid-induced calcium influx in human platelets comparison with the effect of thrombin", Biochem. J, 272(2): 435-443 (1990).

Bennett, et al., "Structure and function of the platelet integrin αIIbβ3", J. Clin. Invest., 115(12): 3363-3369 (2005).

Birschmann, et al., "Ambient hemolysis and activation of coagulation is different between HeartMate II and HeartWare left ventricular assist devices", J. Hear. Lung Transplant., 33(1): 80-87 (2014).

Brown et al., "Response of human platelets to sheer stress", Trans. Am. Soc. Artif. Intern. Organs, 21:35-9 (1975).

Delaney, et al., "Agonist-induced platelet procoagulant activity requires shear and a Rac1-dependent signaling mechanism," Blood, 124(12): 1957-1967 (2014).

Demchenko, "Beyond annexin V: fluorescence response of cellular membranes to apoptosis", Cytotechnology, 65(2): 157-72 (2013).

Dimasi, et al., "Microfluidic flow-based platforms for induction and analysis of dynamic shear-mediated platelet activation—initial validation versus the standardized hemodynamic shearing device", Biomicrofluidics, 12(042208):042208-1-042208-14 (2018).

Himmelreich, et al., "Pathophysiologic role of contact activation in bleeding followed by thromboembolic complications after implantation of a ventricular assist device", ASAIO J., 41(3): M790-4 (1995).

Houël, et al., "Platelet activation and aggregation profile in prolonged external ventricular support", J. Thorac. Cardiovasc. Surg., 128:197-202 (2004).

Hsu, et al., "Bruton's Tyrosine Kinase mediates platelet receptor-induced generation of microparticles: A potential mechanism for amplification of inflammatory responses in rheumatoid arthritis synovial joints", Immunol, Lett., 150(1-2): 97-104 (2013).

Hu, et al., "Lipid profile of platelets and platelet-derived microparticles in ovarian cancer", BBA Clin., 6: 76-81 (2016).

International Search Report and Written Opinion for PCT application PCT/US2019/037528 dated Nov. 5, 2019.

Jesty, et al., "Acetylated Prothrombin as a Substrate in the Measurement of the Procoagulant Activity of Platelets: Elimination of the Feedback Activation of Platelets by Thrombin", Anal. Biochem., 272(1):64-70 (1999).

Jesty, et al., "Platelet activation in a circulating flow loop: combined effects of shear stress and exposure time", Platelets, 14(3): 3143-149 (2003).

Koster, et al., "Alterations in coagulation after implantation of a pulsatile Novacor LVAD and the axial flow MicroMed DeBakey LVAD", Ann. Thorac. Surg., 70(2): 533-7 (2000).

Leung, et al., "Dielectrophoresis-Mediated Electrodeformation as a Means of Determining Individual Platelet Stiffness", Ann Biomed Eng., 44(4):903-13 (2016).

Löffler, et al., "Evaluation of platelet activation in patients supported by the Jarvik 2000* high-rotational speed impeller ventricular assist device", J. Thorac. Cardiovasc. Surg., 137 (3): 736-741 (2009).

Nobili et al., "Platelet activation due to hemodynamic shear stresses: damage accumulation model and comparison to in vitro measurements", ASAIO J., 54(1): 64-72 (2008).

Radovancevic, et al., "Increased leukocyte-platelet interactions during circulatory support with left ventricular assist devices", ASAIO J., 55(5):459-464 (2009).

Ramström, et al., "Platelet phosphatidylserine exposure and procoagulant activity in clotting whole blood—different effects of collagen, TRAP and calcium ionophore A23187", Thromb. Haemost., 89(1):132-41 (2003).

Roka-Moiia, et al., "Platelet Activation via Shear Stress Exposure Induces a Differing Pattern of Biomarkers of Activation versus Biochemical Agonists", Cellular Haemostatis and Platelets, 120(5):776-792 (2020).

Rubenstein, et al., "Differences between mainstream and sidestream cigarette smoke extracts and nicotine in the activation of platelets under static and flow conditions", Circulation, 109(1):78-83 (2004).

Sampaio, et al., "Membrane lipidome of an epithelial cell line", PNAS, 108(5): 1903-1907 (2011).

Schulz-Heik, et al., "The Extent of Platelet Activation under Shear Depends on Platelet Count: Differential Expression of Anionic Phospholipid and Factor Va", Pathophysiolo 34(6): 255-262 (2006).

Shai, et al., "Comparative analysis of platelet-derived microparticles reveals differences in their amount and proteome depending on the platelet stimulus", J. Proteom., 76 Spec No. 287-296 (2012).

Slaughter, et al., "Platelet Activation in Heart Failure Patients Supported by the HeartMate II Ventricular Assist Device", Int. J. Artif. Organs, 34(6): 461-468 (2011).

Staben, et al., "Particle transport in Poiseuille flow in narrow channels" Intl J Multiphase Flow, 31:529-47 (2005).

Starling, et al., "Unexpected abrupt increase in left ventricular assist device thrombosis", N. Engl. J. Med., 370(1): 33-40 (2014).

Sweedo, et al., "Shear-Mediated Platelet Activation is Accompanied by Unique Alterations in Platelet Release of Lipids", Cellular and Molecular Bioengineering, 14(6):597-612 (2021).

Valerio, et al., "Routine clinical anti-platelet agents have limited efficacy in modulating hypershear- mediated platelet activation associated with mechanical circulatory support", Thromb Res., 163:162-171 (2018).

Van Der Meijden, et al., "Platelet P2Y12 receptors enhance signalling towards procoagulant activity and thrombin generation. A study with healthy subjects and patients at thrombotic risk", Thromb. Haemost., 93(6):1128-1136 (2005).

Weyant, et al., "Colon cancer chemoprotective drugs modulate integrin-mediated signaling pathways", Clin Cancer Res, 6:949 (2000).

Wolfs, et al., "Activated scramblase and inhibited aminophospholipid translocase cause phosphatidylserine exposure in a distinct platelet fraction", C. Cell. Mol. Life Sci, 62(13): 1514-1525 (2005).

* cited by examiner

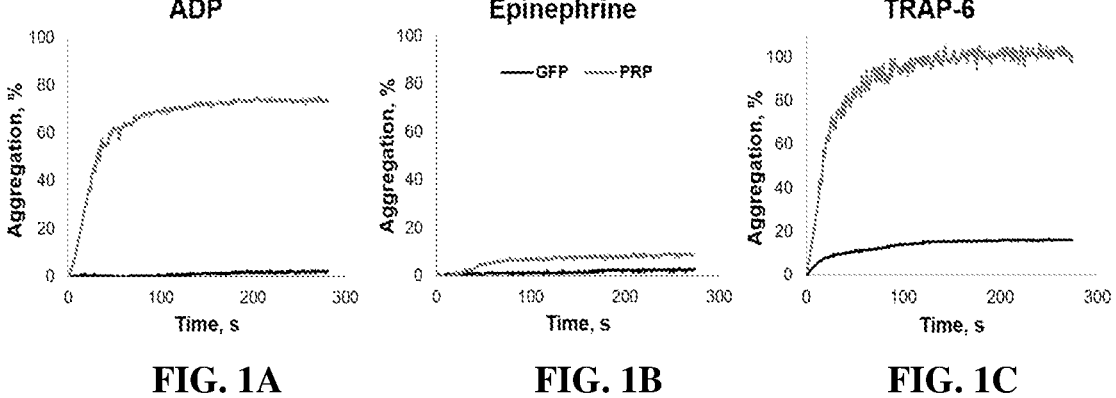
FIG. 1A          FIG. 1B          FIG. 1C
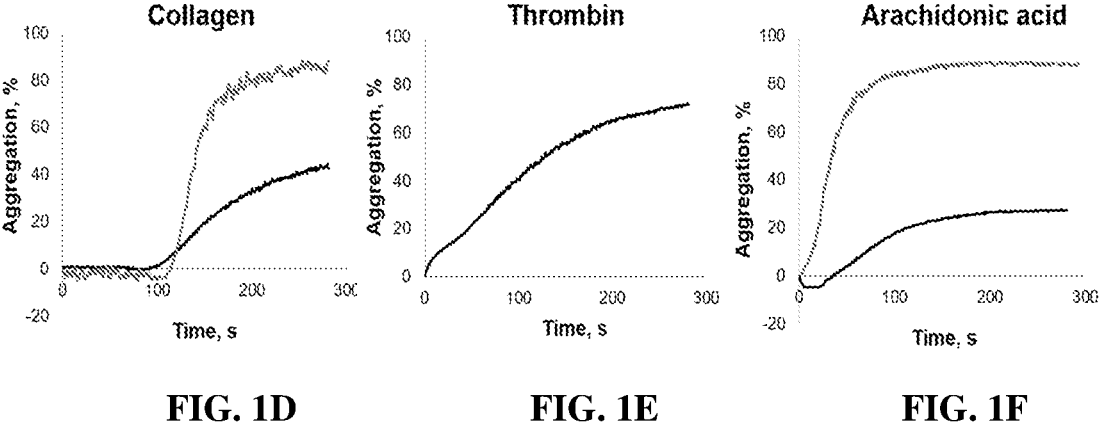
FIG. 1D          FIG. 1E          FIG. 1F

FIG. 2F
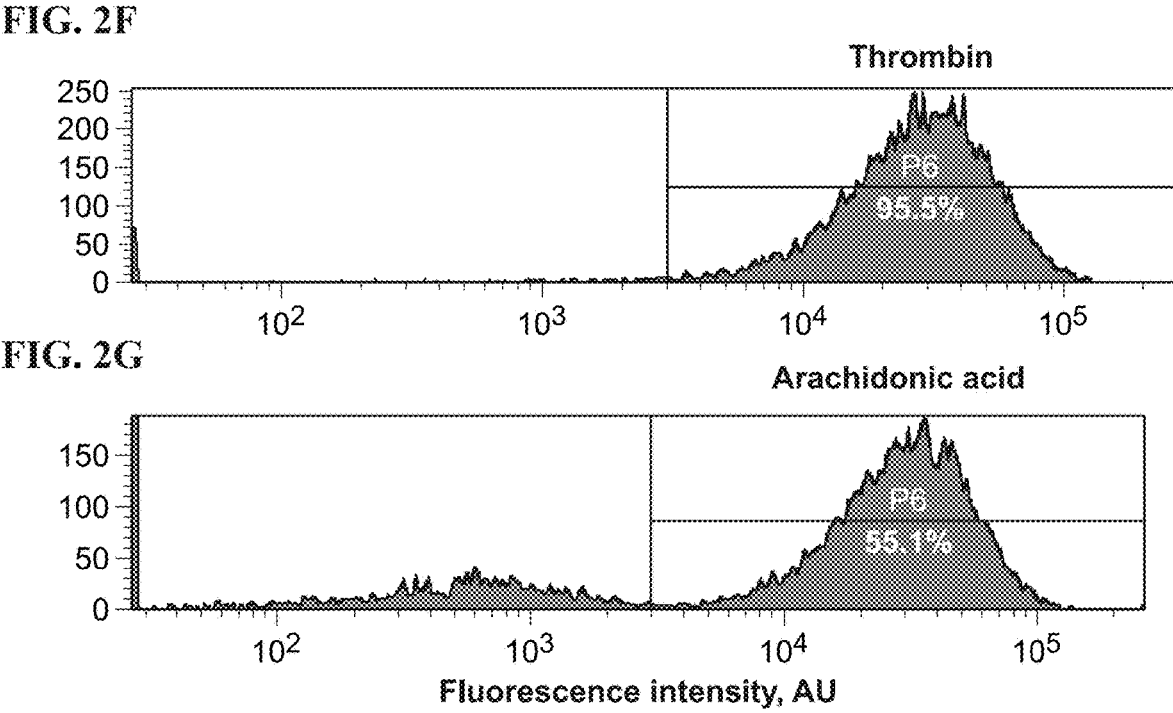
FIG. 2G
FIG. 2H
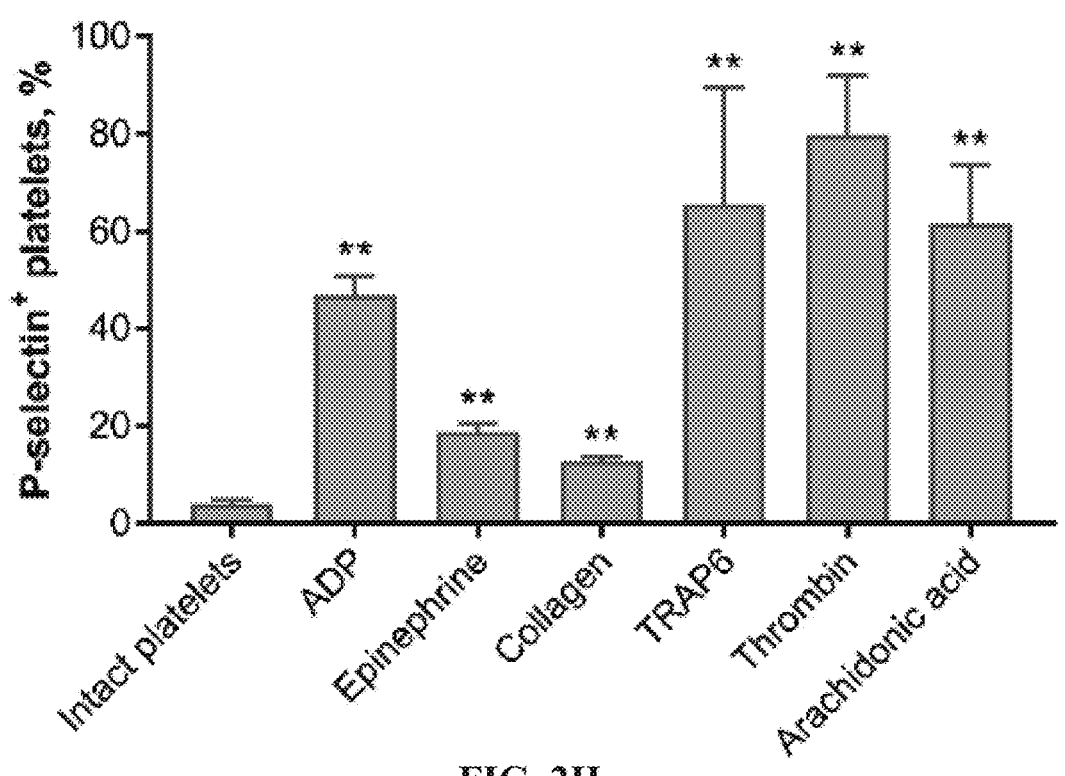

Intact platelets

P6
3.6%

Shear 30 dyn/cm²

P6
12.3%

Shear 50 dyn/cm²

P6
18.1%

Shear 70 dyn/cm²

P6
21.0%

Sonication

P6
20.5%

Fluorescence intensity, AU

FIG. 4F
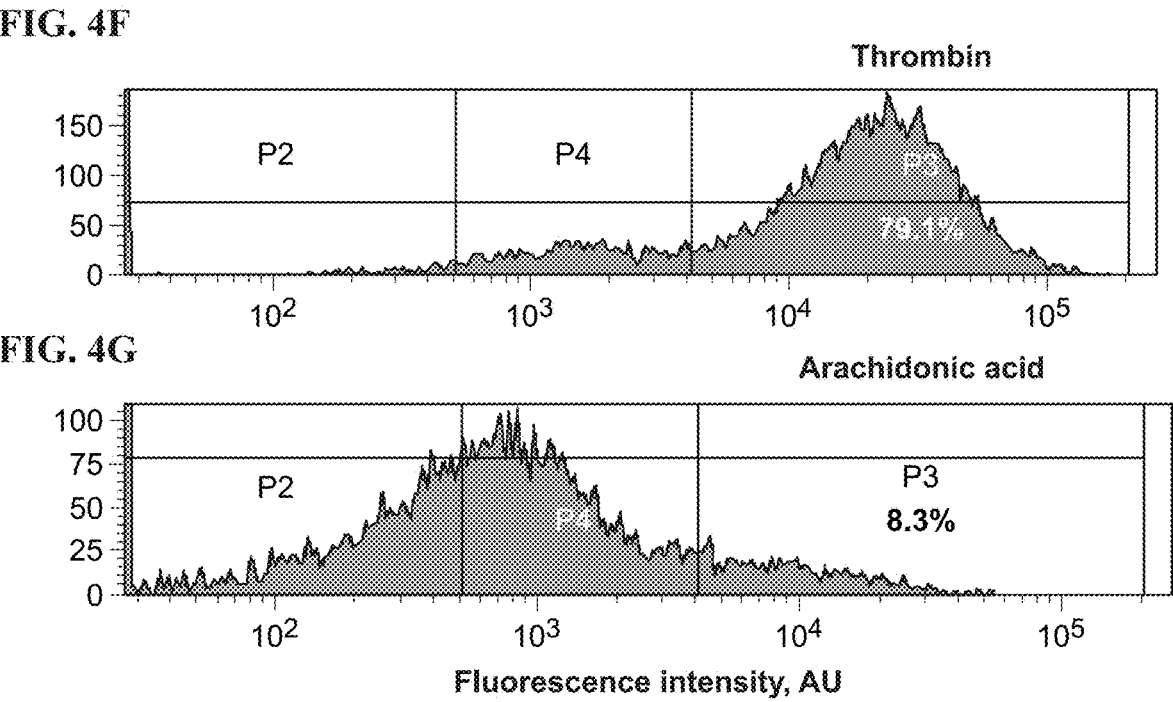
FIG. 4G
FIG. 4H
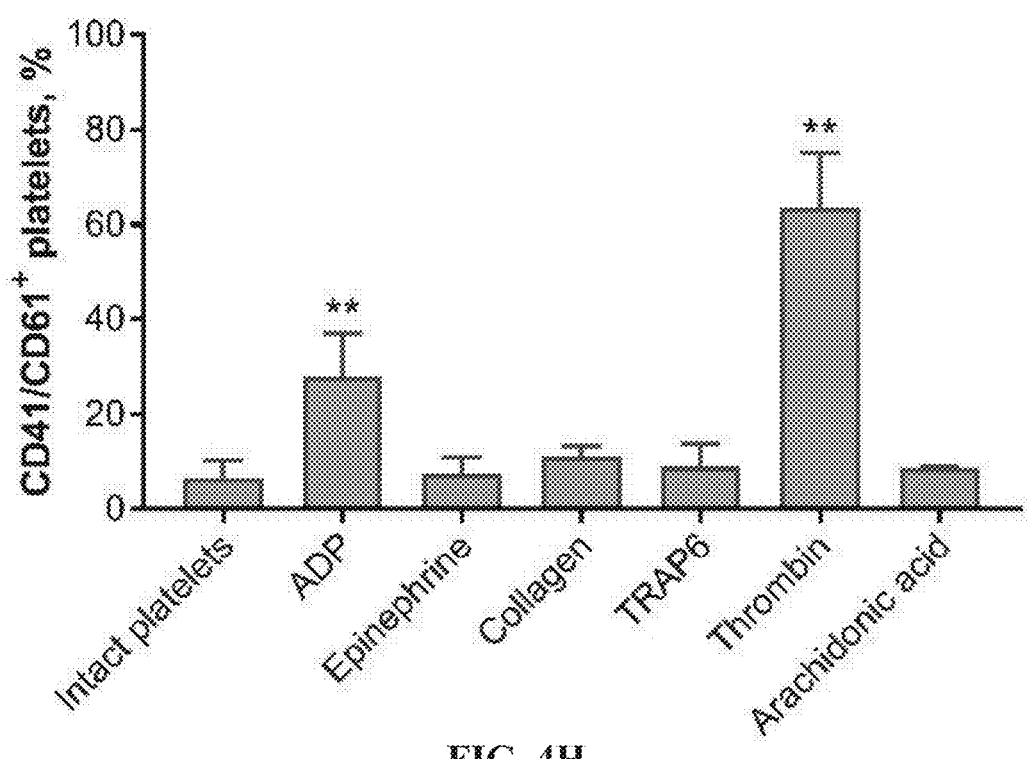

FIG. 7A Intact platelets

FIG. 7B ADP

FIG. 7C Epinephrine

FIG. 7D Collagen

FIG. 7E TRAP-6

Fluorescence intensity, AU

FIG. 7F
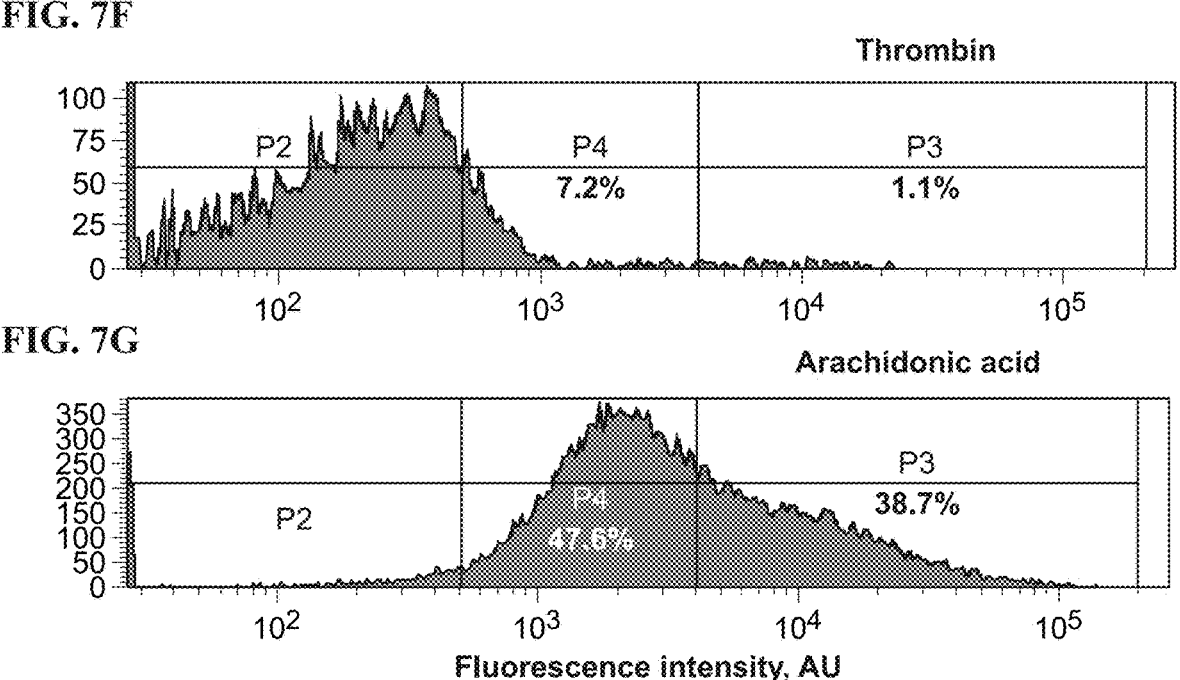
FIG. 7G
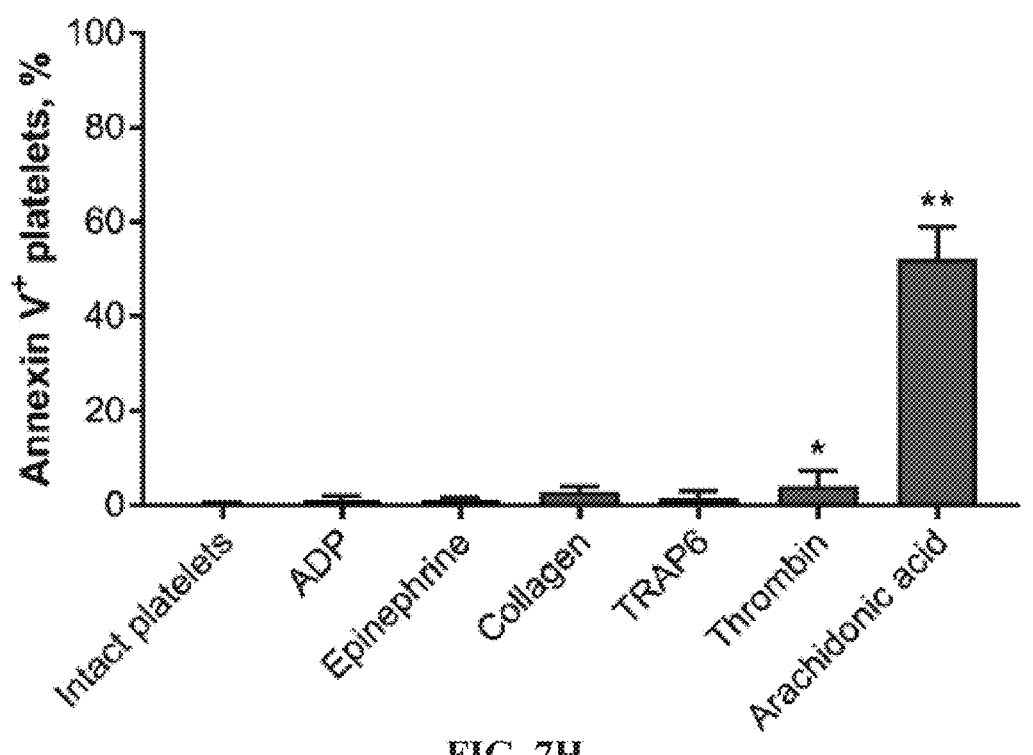
FIG. 7H

METHODS OF DETECTION OF MECHANICALLY-ACTIVATED PLATELET ACTIVATION AND USES THEREOF

CROSS-REFERENCE TO RELATED APPLICATIONS

This application is a National Phase application under 35 U.S.C. § 371 of PCT/US2019/037528, filed Jun. 17, 2019, which claims the benefit of and priority to U.S. Ser. No. 62/685,703 filed Jun. 15, 2018, which are hereby incorporated by reference in their entirety.

STATEMENT REGARDING FEDERALLY SPONSORED RESEARCH

This invention was made with government support under Grant Nos. U01 HL131052 and U01 EB012487, awarded by National Institutes of Health. The government has certain rights in the invention.

FIELD OF INVENTION

The present invention relates to the field of cardiology.

BACKGROUND OF THE INVENTION

Mechanical circulatory support (MCS) in form of ventricular assist devices (VADs) and total artificial hearts is utilized as bridging-to decision, recovery and destination life-support therapy of advanced heart failure. MCS while clinically effective remains limited by thrombotic complications, such as ischemic stroke and pump thrombosis, driven by mechanical platelet activation under extremely high shear stress (up to 10000 s$^{-1}$) existing within VAD-operated blood flow. Pump thrombosis, being complex to diagnose and requiring aggressive clot prevention therapy, carries significant morbidity and leads to multiple readmission and reoperations. According to INTERMACS annual report, pump replacement markedly reduced life-expectancy for 1-year survivals of 65% after the second implant and only 50% after the third implant (Starling et al., *N. Engl. J. Med.*, vol. 370, no. 1, pp. 33-40, January (2014)).

Beyond blood contact with foreign surfaces, MCS device-related thrombosis is mainly potentiated by supraphysiological flow phenomena that promotes thrombus formation via direct mechanical activation of circulating platelets in free flow.

A variety of platelet responses are reported to be driven by high shear stress, e.g. von Willebrand factor (vWF) binding and integrin αIIbβ3 activation, signal transduction and platelet shape change, and releasing of secretory granules and platelet aggregation. According to traditional paradigm of arterial thrombogenesis as thrombus formation in high shear environment, shear-triggered vWF binding to glycoprotein (GP) complex Ib-IX-V is needed for initialization of rapid platelet adhesion under elevated blood flow, subsequent αIIbβ3 activation and stabilization of platelet aggregates. GPIb-IX-V complex is considered to play a principal role in transmembrane transduction of mechanical activation signal inside the cell. Representing some similarities with classic biochemical activation, SMPA indeed results in other dramatic events more likely to be pro-apoptotic. Pathological shear levels (over 100 dyn/cm$^2$) were demonstrated to cause platelet caspase activation, mitochondrial potential dissipation, plasmatic membrane depolarization, cell shrinkage and fragmentation (Brown et al., *Trans. Am. Soc. Artif.*

*Intern. Organs*, vol. 21, pp. 35-9, (1975)). Over the last few years understanding of SMPA phenomena have been expanded beyond the boundaries of a platelet mechanical damage theory. Even so, the molecular mechanisms of mechanoreception and intracellular mechanotransduction of the signal triggering SMPA, as well as the holistic picture of events underlying SMPA by itself are not fully understood.

To evaluate platelet function alterations in patients with MCS, a standard panel of platelet activation markers are monitored, among them membrane integrins (αIIbβ3, GP Ib, CD31) exposed on platelet surface and secretory granule proteins (platelet factor 4, β-thromboglobulin, membrane bound and soluble forms of P-selectin & CD40) released after their activation.

Currently, observations from the clinical experience are controversial and no specific molecular marker of SMPA correlating with platelet function tests and thrombotic outcomes has been reported. For instance, early studies of bridging patients with either pulsatile (Berlin Heart and Novacor system) or axial flow (MicroMed DeBakey) LVADs have indicated that increased platelet factor 4 and β-thromboglobulin levels, which are similar to coagulation parameters within late post-operative period, corresponded to thromboembolic events reported later on (Himmelreich et al., *ASAIO J.*, vol. 41, no. 3, pp. M790-4, Koster et al., *Ann. Thorac. Surg.*, vol. 70, no. 2, pp. 533-7, August (2000)). After external LVAD (Thoratec Corp.) implantation, the platelet surface P-selectin expression remained increased, indicating persistent platelet activation, but GP Ib and GP IIbIIIa activation levels were unaffected (Mi Houël et al., "Platelet activation and aggregation profile in prolonged external ventricular support)).

Independently of length of support, anti-platelet and anti-coagulant regiments, axial flow VADs Jarvik 2000* and HeartMateII implanted for destination therapy did not cause detectable increase in soluble platelet activation markers (P-selectin and CD40 ligand) even considering high rotational speed of the devices (Löffler et al., *J. Thorac. Cardiovasc. Surg.*, vol. 137, no. 3, pp. 736-741, March (2009), Slaughter et al., *Int. J. Artif. Organs*, vol. 34, no. 6, pp. 461-468, June (2011)). In contrast, other studies examined platelet functions during HeartMate II and HeartWare long-term support, which did not find differences in CD41, CD42 and CD62 levels; whereas platelet aggregation and VASP phosphorylation level, as platelet reactivity index, were reportedly significantly increased (Birschmann et al., *J. Hear. Lung Transplant.*, vol. 33, pp. 80-87, (2014)). Summarizing clinical observation, the assessment of known platelet activation markers during MCS failed to reflect platelet function alterations caused by VAD-modified shear conditions. Despite of anticoagulant and antithrombotic interventions, those functional tests still indicate platelet activation and coagulation intensification which might pre-requisite/contribute (to) device-related thrombotic events occurred afterwards.

To date, conventional assays of platelet activation have limited ability to detect early platelet function alterations due to mechanical activation and to distinguish such alterations from those associated with biochemical platelet activation by soluble agonists and adhesive proteins. So far, no specific molecular marker of SMPA correlating with platelet function tests and post-implantation thrombotic outcomes has been reported (A. Koster et al., Ann. Thorac. Surg., 70(2):533-7 (2000), R. Mi Houël et al., J Thorac Cardiovasc Surg. 128(2):197-202 (2004). R. Radovancevic et al., ASAIO J. 55(5):459-464 (2009), C. Löffler et al., J. Thorac. Cardiovasc. Surg., 137(3):736-741 (2009), M. S. Slaughter, et al., Int. J. Artif. Organs, 34(6):461-468 (2011), I. Birschmann et al., J. Hear. Lung Transplant, 33:80-87 (2014)). Currently, non-specific targeting of multiple signaling pathways of platelet biochemical activation by traditional anti-platelet therapeutics within antithrombotic regiments provides no benefits or even causes side-effect associated comorbidity in VAD-supported patients.

There is a need for methods for prediction of device-related thrombosis. There is a need for methods to accurately monitor of antithrombotic therapy for VAD-supported patients.

Therefore, it is an object of the invention to provide methods for monitoring platelet activation pathways, particularly those associated with mechanically-mediated platelet activation.

It is an object of the invention to provide platelet activation pathways and biomarkers that can be used for diagnostic and therapeutic purposes.

It is a further object of the invention to provide improved methods for monitoring the disease activities and responses to treatment for subjects with VADs.

SUMMARY OF THE INVENTION

Biochemical markers that can be measured to determine the level of mechanical activation of a population of platelets are provided. The markers include (a) phosphatidylserine, (b) thrombin, (c) integrin GPIIb/IIIa, (d) glycoprotein GP Ib, (e) P-selectin; (f) platelet size; (g) microparticle generation, and/or (h) lipidomic profile of the membrane.

Methods of measuring the biochemical markers, and using the measurements to prepare composite molecular signatures of the platelets are also provided. The composites typically include measurements of at least two, at least three, at least four, at least five, at least six, at least seven, or eight of markers (a)-(h).

A molecular signature of mechanically activated platelets typically includes two or more molecular features selected from (a) an elevated phosphatidylserine level on the external surface of the platelets relative to a level of a control; (b) an elevated thrombin level on the external surface of the platelets relative to the level of the control; (c) an integrin GPIIb/IIIa level on the external surface of the platelets, wherein the level is not increased compared to the level of the control; (d) a glycoprotein GP Ib level on the external surface of the platelets, wherein the level is not increased compared to the level of the control; (e) a P-selectin level on the external surface of the platelets, wherein the level is not increased compared to the level of the control; (f) a decrease in platelet size relative to the platelet size of the control; (g) an increase in microparticle generation relative to the microparticle generation of the control; and (h) a change in membrane lipidomic profile compared to the membrane lipidomic profile of the control.

The disclosed markers, measurement thereof, and signatures composed therefrom can be used in a variety of methods of patient selection, treatment monitoring, and treatment selection, including both devices and active agents, and methods of treating subjects in need thereof, particularly humans. Examples of such methods are discussed in more detail below and include: reducing shear-activated platelets in the blood of a subject; selecting a blood-contacting medical device for implanting into a subject in need thereof; selecting between two or more medical devices; identifying and optionally treating a subject at a risk of developing a thrombogenic event; monitoring the prophylactic treatment of a subject; selecting a mechanoceutical agent; and delivering an agent to a subject in need thereof.

BRIEF DESCRIPTION OF THE DRAWINGS

FIGS. 1A-1F are line plots showing representative kinetic curves of human platelet aggregation in gel-filtered platelets (GFP) and platelet-rich plasma (PRP) induced by 10 uM ADP (FIG. 1A), 10 µg/mL epinephrine (FIG. 1B), 32 µM TRAP-6 (FIG. 1C), 1 U/mL thrombin (FIG. 1D), 100 µg/mL collagen (FIG. 1E) and 1 mM arachidonic acid (FIG. 1F).

FIGS. 2A-2H are graphs showing human platelet P-selectin exposure induced by biochemical activation: FIGS. 2A-2G are representative flow cytometry histogram plots showing distribution of platelet P-selectin exposure detected by anti-CD62P-APC staining in intact platelets ($20\times10^3$ cells/µL) (FIG. 2A), in gel-filtered platelets (GFP) incubated with ADP (FIG. 2B), epinephrine (FIG. 2C), collagen (FIG. 2D), TRAP-6 (FIG. 2E), thrombin (FIG. 2F), and arachidonic acid (FIG. 2G), along with 2.5 mM $CaCl_2$) undisturbed for 10 min at room temperature. CD62P-positive platelets were marked as P6 population. The number of P6 populations of 4 independent experiments with different donors are summarized, mean value+/−margins of error as error bars are plotted in the bar graph (FIG. 2H). P values were calculated vs intact platelets by one-way ANOVA: *-p≤0.05, **-p≤0.01; for bars without asterisks, p>0.05.

FIGS. 3A-3E are representative flow cytometry histogram plots showing distribution of platelet P-selectin exposure detected by anti-CD62P-APC staining in intact platelets (FIG. 3A), in GFP ($20\times10^3$ cells/µL) sheared utilizing the hemodynamic shearing device (HSD) constant modes 30 dynes/cm$^2$ (FIG. 3B), 50 dynes/cm$^2$ (FIG. 3C), or 70 dynes/cm$^2$ (FIG. 3D) for 10 min at room temperature, and in the positive control treated with sonication (FIG. 3E). CD62P-positive platelets were marked as P6 population. The number of P6 populations of 6 independent experiments with different donors are summarized, mean value+/−margins of error as error bars are plotted in the bar graph (FIG. 3F). P values were calculated vs intact platelets by one-way ANOVA: *-p≤0.05, **-p≤ 0.01; for bars without asterisks, p>0.05.

FIGS. 4A-4H are graphs showing platelet integrin GPIIb/IIIa-activation induced by biochemical activation: FIGS. 4A-4G are representative flow cytometry histogram plots showing distribution of activated GPIIb/IIIa on gel-filtered platelets (GFP) detected using dual-staining with anti-CD41/CD61-FITC (PAC-1 clone, designed against the epitope that appears after GPIIb/IIIa activation) & anti-CD41-APC (against αIIb, exposed in non-activated and activated integrin) in intact platelets (FIG. 4A), in GFP ($20\times10^3$ cells/µL) incubated with ADP (FIG. 4B), epinephrine (FIG. 4C), collagen (FIG. 4D), TRAP-6 (FIG. 4E), thrombin (FIG. 4F), and arachidonic acid (FIG. 4G), along with 2.5 mM $CaCl_2$) undisturbed for 10 min at room temperature. Percentage of CD41/CD61-positive platelets out of total CD41-positive platelets is marked as P3 population. The number of P6 populations of 6 independent experiments with different donors are summarized, mean value+/−margins of error as error bars are plotted in the bar graph (FIG. 4H). P values were calculated vs intact platelets by one-way ANOVA: *-p≤0.05, **-p<0.01; for bars without asterisks, p>0.05.

FIGS. 5A-5E are representative flow cytometry histogram plots showing distribution of GPIIb/IIIa of gel-filtered platelets (GFP) detected using dual-staining with anti-CD41/CD61-FITC (PAC-1 clone, designed against the epitope that appears after GPIIb/IIIa activation) & anti-CD41-APC (against αIIb, exposed in non-activated and activated integrin) in intact platelets (FIG. 5A), in GFP ($20 \times 10^3$ cells/μL) sheared utilizing HSD constant modes 30 dynes/cm$^2$ (FIG. 5B), 50 dynes/cm$^2$ (FIG. 5C), or 70 dynes/cm$^2$ (FIG. 5D) for 10 min at room temperature, and in the positive control treated with sonication (FIG. 5E). Percentage of CD41/CD61-positive platelets out of total CD41-positive platelets is marked as P3 population. P6 populations of 6 independent experiments with different donors are summarized, mean value+/−margins of error as error bars are plotted in the bar graph (FIG. 5F). P values were calculated vs intact platelets by one-way ANOVA: *-p≤0.05, **-p≤0.01; for bars without asterisks, p>0.05.

FIGS. 7A-7H are graphs showing human platelet phosphatidylserine (PS) externalization induced by biochemical activation: FIGS. 7A-7G are representative flow cytometry histogram plots showing distribution of platelet PS externalization detected using FITC-bound annexin V in intact platelets (FIG. 7A), in GFP ($20 \times 10^3$ cells/μL) incubated with ADP (FIG. 7B), epinephrine (FIG. 7C), collagen (FIG. 7D), TRAP-6 (FIG. 7E), thrombin (FIG. 7F), and arachidonic acid (FIG. 7G), along with 2.5 mM CaCl$_2$) undisturbed for 10 min at room temperature. Annexin V-positive platelets was marked as P3 population. The number of P3 populations of 6 independent experiments with different donors are summarized, mean value+/−margins of error as error bars are plotted in the bar graph (FIG. 7H). P values were calculated vs intact platelets by one-way ANOVA: *-p≤0.05, **-p≤0.01; for bars without asterisks, p>0.05.

FIGS. 8A-8E are representative flow cytometry histogram plots showing distribution of platelet PS externalization detected using FITC-bound annexin V in intact platelets (FIG. 8A), in GFP ($20 \times 10^3$ cells/μL) sheared utilizing HSD constant modes 30 dynes/cm$^2$ (FIG. 8B), 50 dynes/cm$^2$ (FIG. 8C), or 70 dynes/cm$^2$ (FIG. 8D) for 10 min at room temperature, and in the positive control treated with sonication (FIG. 8E). Annexin V-positive platelets were marked as P3 population. The number of P3 populations of 8 independent experiments with different donors are summarized, mean value+/−margins of error as error bars are plotted in the bar graph (FIG. 8F). P values were calculated vs intact platelets by one-way ANOVA: *-p≤0.05, **-p≤0.01; for bars without asterisks, p>0.05. FIG. 8G is a bar graph showing the mean fluorescent intensity (MFI) of intact platelets, shear-treated, and sonicated platelets ("70 dynes/cm2" vs. "Intact platelets", ANOVA p<0.01).

DETAILED DESCRIPTION OF THE INVENTION

Figures 2A, 2B, 2C, 2D, 2E:
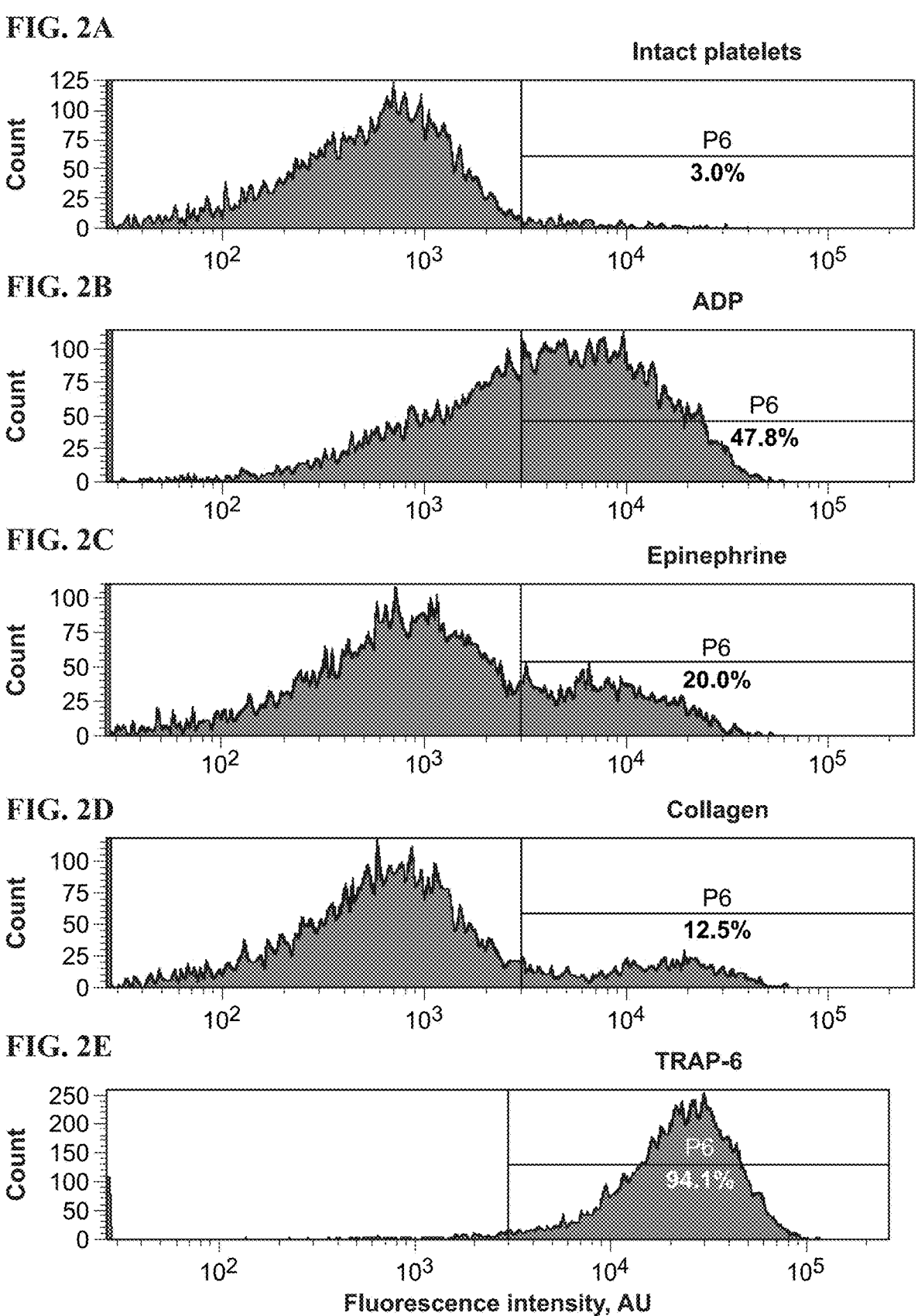
Figures 3A, 3B, 3C, 3D, 3E:
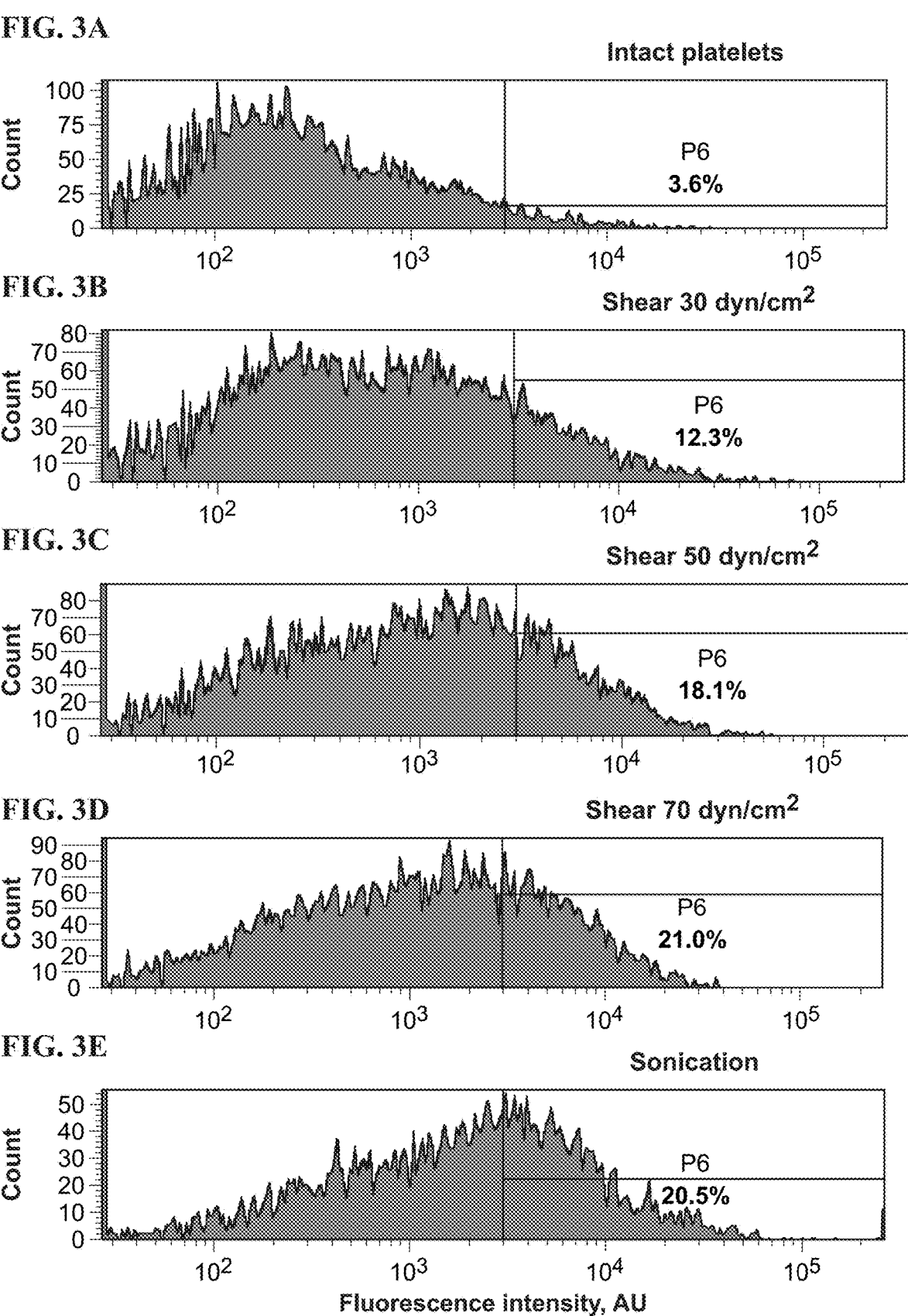
FIGS. 3A-3F are graphs showing human platelet P-selectin exposure induced by constant uniform shear.
Figure 3F:
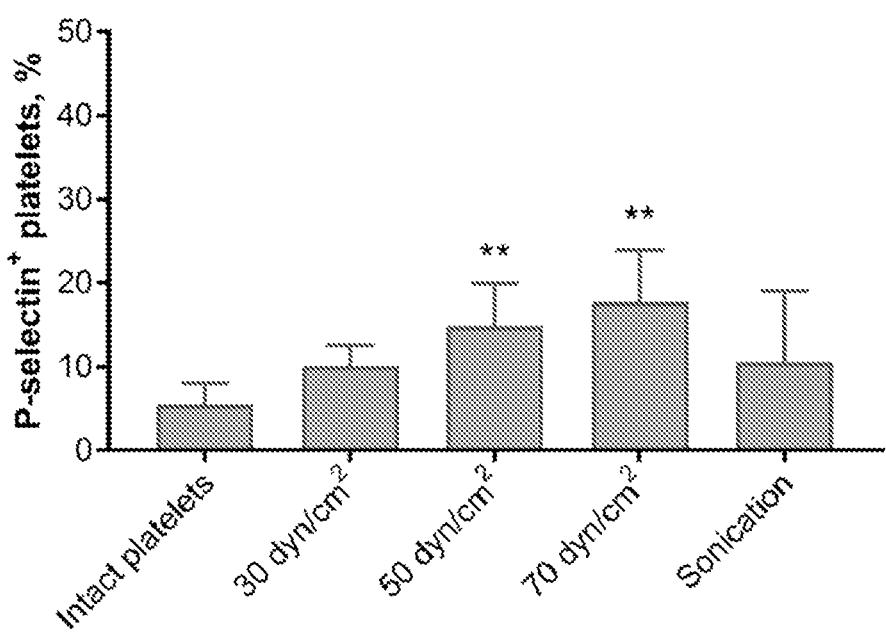

Medical diagnosis involves consideration of a composite of biomarkers. It has been found that significant differences in certain biomarkers are associated with mechanically-activated platelets compared to biochemical platelet activation by known biochemical agonists. While a diagnosis of the cause of a thrombogenic response in a subject can be made using only two of the biomarkers described herein, the sensitivity of the diagnosis increases the greater the number of biomarkers that are present.

Platelets can be mechanically activated by a variety of mechanical actions including shear, vibration, audible sound, ultrasound, acoustic stimulation, pressure, or long-term storage in blood bank environment.

Biomarkers for mechanically-activated platelets include one or more of the following: an elevated phosphatidylserine level on the external surface of the platelets relative to a level of a control; an elevated thrombin level on the external surface of the platelets relative to the level of the control; an integrin GPIIb/IIIa level on the external surface of the platelets and GPIIb/IIIa activation level, wherein these levels are not increased compared to the level of the control; a glycoprotein GP Ib level on the external surface of the platelets, wherein the level is not increased compared to the level of the control; a P-selectin level on the external surface of the platelets, wherein the level is not increased compared to the level of the control.

Additional indicators of the presence of a population of mechanically-activated platelets include one or more of the following: significant (or excessive) microparticle generation, change of lipidomic profile of the membrane (increase and decrease of specific lipid species), early change in average platelet shape, and decrease in average platelet size relative to a control.

I. Definitions

The term "microfluidic device" refers to a device comprising fluidic structures and internal channels having microfluidic dimensions. These fluidic structures may include chambers, valves, vents, vias, pumps, inlets, nipples, and detection means, for example. Generally, microfluidic channels are fluid passages having at least one internal cross-sectional dimension that is less than approximately 500 μm to 1000 μm and typically between approximately 0.1 μm and approximately 500 μm. The microfluidic flow regime is characterized by "Poiseuille" or "laminar" flow (see, e.g., Staben et al. (2005) "Particle transport in Poiseuille flow in narrow channels" Intl J Multiphase Flow 31:529-47, and references cited therein).

The term "mechanoceuticals" are generally molecules that alter one or more physical properties of a cell (e.g., a platelet), including but not limited to membrane fluidity/stiffness/stability, membrane function, intracellular microfilament function, intracellular microtubule function, intracellular fluid content and tonicity, and submembrane assemblies.

II. Molecular Signatures of Mechanically Activated Platelets

Molecular signatures of mechanically activated platelets are described. Platelets can be activated by chemical or mechanical stimuli. Exemplary mechanical stimuli are shear, vibration, audible sound (ultrasound), acoustic stimulation, pressure, and a combination thereof.

Shear-mediated platelet activation (SMPA) is central in thrombosis of implantable cardiovascular therapeutic devices. Molecular signatures of SMPA are also provided. The terms "resting platelets" and "intact platelets" are used interchangeable herein and generally refer to unactivated platelets.

A. Molecular Markers for Early Platelet Activation Associated with Mechanical Stimuli Molecular markers, also referred to herein as molecular features, for early platelet activation associated with mechanical stimuli are described. The early activation markers can include an elevated level of a negatively charge phospholipids, such as phosphatidylserine and/or phosphatidylethanolamine on the external surface of the platelets. Another early activation marker is an elevated level of thrombin generation on the external surface of the platelets. Optionally, a further early activation marker for SMPA is no or a minimal change in P-selectin level, integrin GPIIb/IIIa level, and/or integrin GPIIb/IIIa activation level compared to a control from a healthy subject with minimal risk of developing thrombosis.

In some embodiments, molecular signatures of mechanically activated platelets include one or more molecular features of (a) an elevated phosphatidylserine level on the external surface of the platelets relative to a level of a control; (b) an elevated thrombin level on the external surface of the platelets relative to the level of the control; (c) an integrin GPIIb/IIIa level on the external surface of the platelets and integrin GPIIb/IIIa activation level, wherein these levels are not increased compared to the level of the control; (d) a glycoprotein GP Ib level on the external surface of the platelets, wherein the level is not increased compared to the level of the control; (e) a P-selectin level on the external surface of the platelets, wherein the level is not increased compared to the level of the control; (f) a decrease in platelet size relative to the platelet size of the control; (g) an increase in microparticle generation relative to the microparticle generation of the control, and (h) a change in membrane lipidomic profile compared to the membrane lipidomic profile of the control.

The disclosed methods can include measuring one or more molecular markers in test platelets and comparing the level of the marker(s) to a control. As illustrated in the experiments below, the disclosed molecular signatures may vary somewhat from cell-to-cell within a population of platelets. Thus, the disclosed molecular signatures are typically used to characterize a population of platelets, rather than an individual isolated platelet. Methods that include measuring one or more molecular markers may include measuring the one or more molecular markers on a test population of platelets and determining the percentage of platelets in the test population that are positive or negative for the one or more molecular markers, and comparing the results to a control population.

Individual platelets can be positive or negative for a particular molecular marker when the platelet's level of expression meets or exceeds a threshold level, or fails to meet or exceed the threshold level, respectively. For example, in the experiments below, the molecular marker on individual platelets is typically measured by flow cytometry. Individual platelets are identified as positive for a molecular marker when the fluorescence intensity indicative of the molecular marker meets or exceeds a threshold level of fluorescence.

Flow cytometry and other means of measuring a marker in non-lysed cells are preferred methods of measuring expression of the disclosed markers, particularly when localization (e.g., to the cell surface) is important for the analysis.

If the percentage of the test population that is positive for the molecular marker is higher than the percentage of the control that is positive for the molecular marker, the marker can be said to be elevated, higher, or increased relative to the control population. If the percentage of the test population that is positive for the molecular marker is lower than the percentage of the control that is positive for the molecular marker, the marker can be said to be lower or decreased relative to the control population.

Molecular markers can also be measured by quantitating the level of the marker(s) in a population. For example, in some embodiments, the level of a molecular marker in a population is determined by measuring its gene or protein expression.

If level of the molecular marker in the test population is higher than the level of the marker in a quantitatively same or similar control population, the marker can be said to be elevated, higher, or increased relative to the control population. If level of the molecular marker in the test population is lower than the level of the marker in a quantitatively same or similar control population, the marker can be said to be lower or reduced relative to the control population.

The control can be a population of resting platelets obtained from a healthy subject with minimal risk of developing thrombosis. In some embodiments, a control is resting platelets isolated from the subject under study. Phenotypes of resting platelets are known in the art, for example, low levels of P-selectin, integrin GPIIb/IIIa activation, phosphatidylserine, thrombin generation, and/or a combination on the external surface.

Additionally or alternatively, the test population can be compared to a population of platelets treated with a chemical activator. The chemical activator can have an effect on the molecular marker relative to a control as described in the disclosure and figures herein. Thus, the molecular signature of a population of stress activated platelets can be distinguished from that of both resting platelets and chemically activated platelets, particularly when the signature is formed of two, three, four, or more markers.

1. Negatively Charged Phospholipids

Platelet membrane reorganization and externalization of negatively charged phospholipids is considered as one of the latest events of platelet activation, known as platelet procoagulant activity. These negatively charged phospholipids, typically including phosphatidylserine and phosphatidylethanolamine, cluster and provide a surface for the assembly of tenase and prothrombinase complexes, and hence catalyze local thrombin generation on the platelet membrane.

Levels of one or more negatively charged phospholipids can be elevated in mechanically activated platelets. For example, the levels of one or more negatively charged phospholipids in the mechanically-activated platelets can be elevated relative to a control, such as a population of resting platelets obtained from a healthy subject with minimal risk of developing thrombosis.

In some embodiments, one or more markers of molecular signatures of mechanically activated platelets include one or more negatively charged phospholipids, for example, phosphatidylserine. In some embodiments, the level of phosphatidylserine in the mechanically-activated platelets is elevated relative to a control. In further embodiments, the level of phosphatidylserine on the external surface of the mechanically activated platelets is elevated than platelets activated by chemical activators such as physiologically relevant soluble agonists e.g., Adenosine DiPhosphate (ADP), epinephrine, thrombin receptor activating peptide-6 (TRAP-6), thrombin, and collagen.

In some embodiments annexin V binding is used to measure phosphatidylserine level. This assay is based on high affinity binding of protein annexin V to phosphatidylserine on platelet surface.

In some embodiments, two subpopulations can be distinguished using an annexin V binding assay: a high annexin V sub-population P3 (fluorescence intensity >4000 AU) and a low annexin V sub-population P4 (fluorescence intensity 500-4000 AU). Thus, in some embodiments, an individual platelet is considered to be positive or high for phosphatidylserine when its fluorescence intensity in an annexin V binding assay is greater than 4000 AU, and negative or low for phosphatidylserine when its fluorescence intensity in an annexin V binding assay is less than or equal to 4000 AU.

In some embodiments, the threshold for low annexin V platelet sub-population is established based on its fluorescence intensity level which must be higher than platelet spontaneous fluorescence (i.e. fluorescence of intact platelet sample to which no fluorescent dye-conjugated annexin V was added).

2. Thrombin Generation from Platelets

In some embodiments, the methods can include measuring thrombin generation on platelet surfaces to monitor platelet procoagulant activity.

Levels of thrombin generation on platelet surfaces can be elevated in mechanically activated platelets. In some embodiments, the level of thrombin in the mechanically-activated platelets is elevated relative to a control, such as a population of resting platelets obtained from a healthy subject with minimal risk of developing thrombosis. In further embodiments, the level of thrombin on the external surface of the mechanically activated platelets is elevated than platelets activated by chemical activators such as physiologically relevant soluble agonists e.g., Adenosine DiPhosphate (ADP), epinephrine, thrombin receptor activating peptide-6 (TRAP-6), thrombin, and collagen.

In some embodiments, thrombin generation rate is measured using a chromogenic prothrombinase-based Platelet Activation State (PAS) assay. The control can be thrombin generation rate on a population of resting platelets obtained from a healthy subject with minimal risk of developing thrombosis. In some embodiments, a control is a thrombin generation rate on resting platelets isolated from the subject under study.

3. Surface Membrane Glycoprotein

In some embodiments, one or more markers of molecular signatures of mechanically activated platelets include one or more integrin of platelets, for example, Glycoprotein Ib (GPIb), also known as CD42.

In some embodiments, the expression level of GPIb on the external surface of the mechanically activated platelets is reduced compared to expression level of GPIb of resting platelets, for example, 5%, 10%, 15%, and 20%.

In preferred embodiments, the of GPIb on the external surface of the mechanically activated platelets is about the same or less than those activated by one or more chemical activators such as physiologically relevant soluble agonists e.g., Adenosine DiPhosphate (ADP), epinephrine, thrombin receptor activating peptide-6 (TRAP-6), thrombin, collagen, and arachidonic acid.

4. Selectins

P-selectin functions as a cell adhesion molecule (CAM) on the surfaces of activated platelets. P-selectin mediates rolling of platelets on activated endothelial cells. After platelet activation, P-selectin is translocated from intracellular granules to the external membrane, whereas fibrinogen aggregates platelets by bridging integrin GPIIb/IIIa between adjacent platelets.

The methods can include measuring the P-selectin level on the surface of platelets activated by shear stress. Levels of P-selectin in a population of platelets that have been exposed to high shear stress can be similar to that of a control, such as a population of resting platelets obtained from a healthy subject with minimal risk of developing thrombosis.

In some embodiments, the expression level of P-selectin on the external surface of the mechanically activated platelets is reduced compared to expression level of P-selectin of resting platelets, for example, 5%, 10%, 15%, and 20%. In some embodiments, the percentage of mechanically activated platelets positive for P-selectin is the same, similar, or only slightly increased relative to the percentage of resting platelets that are P selectin positive, for example, an increase in the P-selectin positive population of 35%, 30%, 25%, 20%, 15%, 10%, 5% or less than 5% relative to the resting platelets population.

In preferred embodiments, P-selectin on the external surface of the mechanically activated platelets is about the same or less than those activated by chemical activators such as physiologically relevant soluble agonists e.g., Adenosine DiPhosphate (ADP), epinephrine, thrombin receptor activating peptide-6 (TRAP-6), thrombin, collagen, and arachidonic.

In some embodiments, P-selectin exposure is detected by flow cytometry. Platelets having high fluorescence intensity can be identified as P-selectin positive platelets. In some embodiments, an individual platelet is identified as P-selectin high or positive when the fluorescence of the individual platelet is greater than or equal to 3000 AU. Similarly, an individual platelet can be identified as negative or low for P-selectin when the fluorescence of the individual platelet is less than 3000 AU.

In some embodiments, the threshold for low P-selectin platelet can be established based on its fluorescence intensity level which must be higher than platelet spontaneous fluorescence (i.e. fluorescence of an intact platelet to which no fluorescent dye-conjugated anti-P-selectin antibody was added).

5. Integrins

Platelets contain five integrins, three $\beta 1$ integrins that mediate platelet adhesion to the matrix proteins collagen, fibronectin and laminin, and the $\beta 3$ integrins $\alpha v \beta 3$ and $\alpha IIb\beta 3$ (J Clin Invest, 2005; 115:3363).

In some embodiments, one or more markers of molecular signatures of mechanically activated platelets include one or more integrins of platelets, for example, glycoprotein IIb/IIIa (GPIIb/IIIa, also known as integrin $\alpha IIb\beta 3$).

In some embodiments, the expression level and/or activation of integrin GPIIb/IIIa on the external surface of the mechanically activated platelets is reduced compared to expression level of integrin GPIIb/IIIa of resting platelets, for example, 5%, 10%, 15%, and 20%.

In some embodiments, the percentage of mechanically activated platelets positive for expression and/or activation of integrin GPIIb/IIIa is the same, similar, or only slightly increased relative to the percentage of resting platelets that are integrin GPIIb/IIIa positive, for example, an increase in the integrin GPIIb/IIIa positive population of 35%, 30%, 25%, 20%, 15%, 10%, 5% or less than 5% relative to the resting platelets population.

In preferred embodiments, the level and/or activation of integrin GPIIb/IIIa on the external surface of the mechanically activated platelets is about the same or less than those activated by one or more chemical activators such as physiologically relevant soluble agonists e.g., Adenosine DiPhosphate (ADP), epinephrine, thrombin receptor activating peptide-6 (TRAP-6), thrombin, collagen, and arachidonic acid.

In some embodiments, GPIIb/IIIa activation is determined by quantifying and comparing the number of all GPIIb/IIIa-positive platelets with the number of platelets presenting the activated form of the integrin on their surface. Within the parental CD41-positive platelet population, CD41/CD61-positive cells can be distinguished. In some embodiments, the populations are distinguished based on their fluorescence intensity. Individuals platelets having fluorescence intensity greater than or equal to 4000 AU are positive for activated GPIIb/IIIa. Individual platelets having less than 4000 AU are negative for activated GPIIb/IIIa.

In some embodiments, the threshold for positive for activated GPIIb/IIIa platelet can be established based on its fluorescence intensity level which must be higher than platelet spontaneous fluorescence (i.e. fluorescence of an intact platelet to which no fluorescent dye conjugated anti-CD41/CD61 antibody was added).

6. Platelet Size and Shape

Figure 6A:
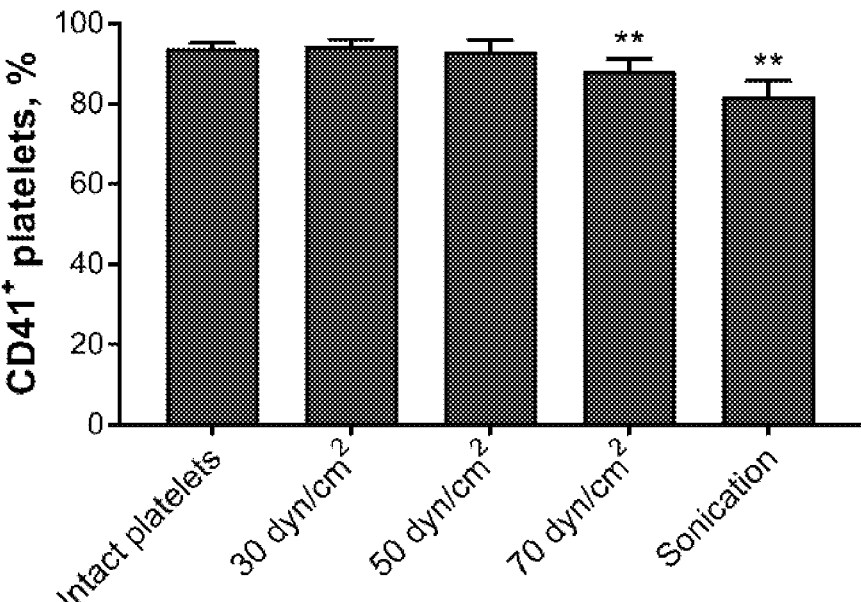
FIGS. 6A-6C are bar graphs showing the number of platelets expressing integrin GPIIb/IIIa (FIG. 6A), platelet fluorescence intensity (FIG. 6B), and size distribution (FIG. 6C) of GFP ($20 \times 10^3$ cells/μL) sheared utilizing HSD constant modes 30, 50, or 70 dynes/cm$^2$ for 10 min at room temperature, and in the positive control treated with sonication. Integrin GPIIb/IIIa expression was detected using anti-CD41-APC. The bar graphs represent 6 independent experiments with different donors, mean value±margins of error as error bars are plotted. P values were calculated vs intact platelets by one-way ANOVA: *-p<0.05, **-p≤0.01; for bars without asterisks, p>0.05.
Figure 6B:
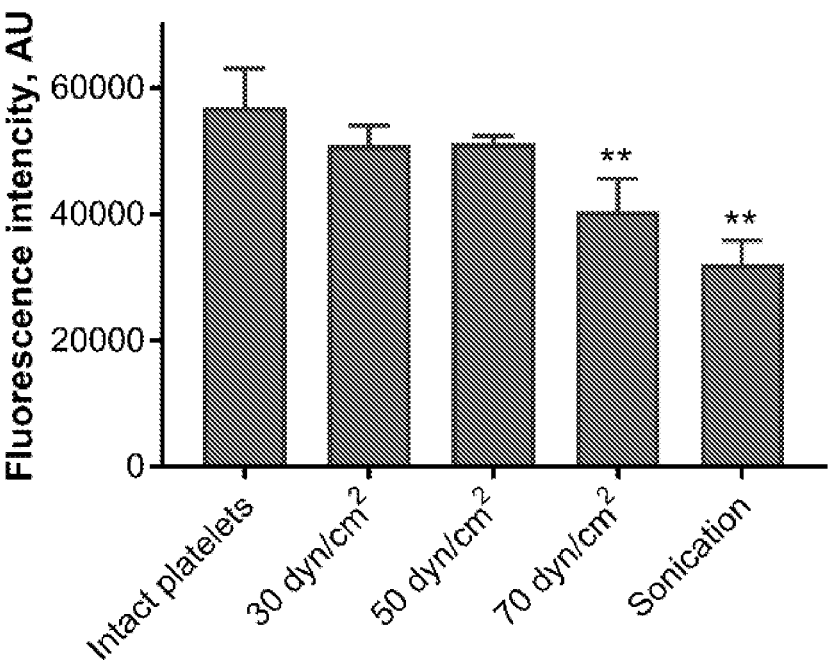
Figure 6C:
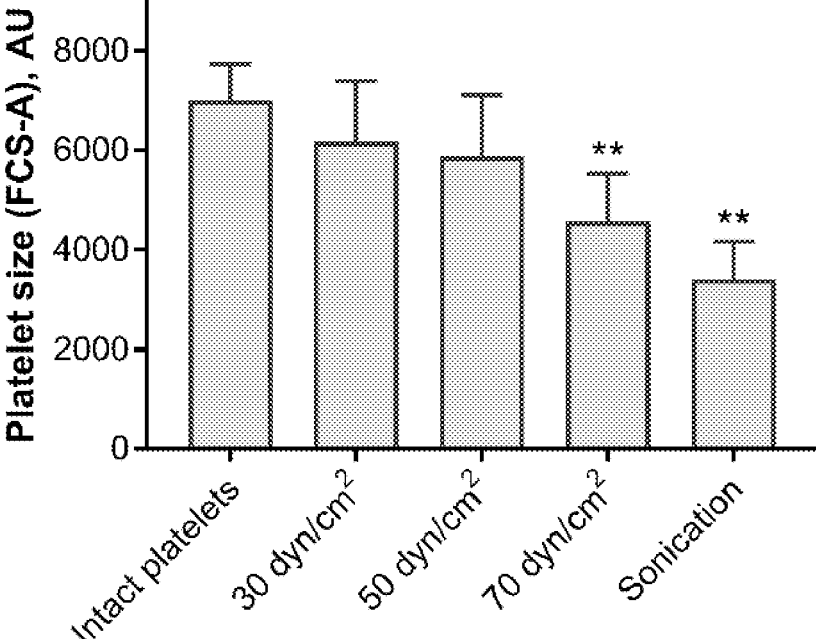

Further changes associated with mechanically activated platelets can also include morphological changes, for example, platelet size and shape. In some embodiments, one or more markers of molecular signatures of mechanically activated platelets include the size and/or shape of platelets. Standard assays for determining size and/or shape of platelets are known in the art, see for example in Example 2 and associated FIG. 6C. Exemplary assays include flow cytometry (e.g., measuring forward scatter and side scatter (FSC-A/SSC-A) characteristics) and microscopy.

In some embodiments, mechanically activated platelets decrease in size compared to resting platelets, for example, by 5%, 10%, 15%, 20%, 30%, 40%, 50%. In some embodiments, the threshold for control platelets size can be established based on FSC-A/SSC-A characteristics of an intact platelet toward which no mechanical or chemical stimuli were applied.

7. Microparticle Generation

Activated platelets vesiculate to produce platelet microparticles (PMPs), a heterogeneous population of small membrane-coated vesicles, ranging from 0.1 to 1.0 $\mu$m in diameter (Shai et al., J. Proteom. 76 Spec No: 287-296 (20120; Hsu et al., Immunol. Lett. 150 97-104 (2013)). In some embodiments, one or more markers of molecular signatures of mechanically activated platelets include microparticle generation. Standard assays for determining microparticle generation of platelets are known in the art. Exemplary assays include flow cytometry (e.g., measuring forward scatter and side scatter (FSC-A/SSC-A) characteristics), microscopy, and density centrifugation.

In some embodiments, mechanically activated platelets increase microparticle generation compared to resting platelets. In some embodiments, mechanically activated platelets increase microparticle generation compared to platelets activated by chemical activators such as physiologically relevant soluble agonists e.g., Adenosine DiPhosphate (ADP), epinephrine, thrombin receptor activating peptide-6 (TRAP-6), thrombin, collagen, and arachidonic acid. In some embodiments, the number of microparticles is considered to be elevated if it exceeds the number of microparticles in an intact platelet sample towards which no mechanical or chemical stimuli were applied.

8. Membrane Lipidomic Profile

Changes in the lipidomic profile of the membrane, i.e, changes in specific lipid composition of the platelet membrane can also occur in mechanically activated platelets. In some embodiments, one or more markers of molecular signatures of mechanically activated platelets include changes in lipidomic profile of platelet membrane. Methods for measuring lipidomic profile have been described in the art, such as shotgun lipidomics using mass spectrometry. See for example, Sampaio J L et al., PNAS Feb. 1, 2011. 108 (5) 1903-1907, and Hu Q et al., BBA Clin. 2016 December; 6:76-81.

Some exemplary lipids for preparing a lipidomic profile of platelets include phosphatidylserine, phosphatidylinositol, phosphatidic acid, phosphatidylglycerol, phosphatidylcholine, acyl-carnitines, and sphingomyelins. In some embodiments, mechanically activated platelets have a changed composition (e.g., membrane composition) of one or more lipids of phosphatidylserine, phosphatidylinositol, phosphatidic acid, phosphatidylglycerol, phosphatidylcholine, acyl-carnitines, and sphingomyelins, relative to, for example resting platelets and/or platelets activated by one or more chemical activators. In some embodiments, C20 lipids, arachidonate precursors, or a combination thereof are altered in activated platelets.

III. Methods

Methods for creating a molecular signature of mechanically-activated platelets and methods of using the molecular signature of mechanically-activated platelets are described. The molecular biomarkers of mechanically-activated platelets can be used to guide diagnostic and therapeutic therapy, or in monitoring the disease activities and responses to treatment.

A. Methods of Creating A Molecular Signature of Mechanically-Activated Platelets Methods of creating a molecular signature of mechanically-activated platelets are provided. In some embodiments, the methods of creating a molecular signature of platelets activated by one or more mechanical stimuli include measuring a composite of at least two of (a) phosphatidylserine, (b) thrombin, (c) integrin GPIIb/IIIa activation, (d) glycoprotein GP Ib, (e) P-selectin; (f) platelet size; (g) microparticle generation, and (h) lipidomic profile of the membrane, preferably at least three of (a)-(h), at least four of (a)-(h), at least five of (a)-(h), at least six of (a)-(h), at least seven of (a)-(h), and all of (a)-(h). In some embodiments, the platelets are isolated from a blood sample of a subject.

Methods for identifying cause or mechanism of platelet activation are also described. Particularly, methods of early identification of platelets activated by one or more mechanical stimuli are described. In some embodiments, platelets are identified as activated by one or more mechanical stimuli, not physiologically relevant soluble agonists e.g., Adenosine diphosphate (ADP), epinephrine, TRAP-6, thrombin, collagen, and arachidonic acid if the platelets have a molecular signature including one or more molecular features of (a) an elevated phosphatidylserine level on the external surface of the platelets relative to a level of a control; (b) an elevated thrombin level on the external surface of the platelets relative to the level of the control; (c) an integrin GPIIb/IIIa level on the external surface of the platelets, wherein the level is not increased compared to the level of the control; (d) a glycoprotein GP Ib level on the external surface of the platelets, wherein the level is not increased compared to the level of the control; (e) a P-selectin level on the external surface of the platelets, wherein the level is not increased compared to the level of the control; (f) a decrease in platelet size relative to the platelet size of the control; (g) an increase in microparticle generation relative to the microparticle generation of the control, and (h) a change in membrane lipidomic profile compared to the membrane lipidomic profile of the control. In preferred embodiments, platelets are identified as activated by one or more mechanical stimuli, not physiologically relevant soluble agonists if the platelets have a molecular signature including at least three of (a)-(h), at least four of (a)-(h), at least five of (a)-(h), at least six of (a)-(h), at least seven of (a)-(h), and all of (a)-(h).

B. Methods of Diagnosing

In some embodiments, the disclosed methods are utilized to diagnose a subject at risk of developing thrombotic events. In preferred embodiments, the disclosed methods are utilized to diagnose a subject at risk of developing thrombotic events from mechanically activated platelets.

In some embodiments, methods for identifying a subject at a risk of developing a thrombotic event include the steps of (a) creating a molecular signature of the platelets in the blood sample collected from a subject according to claim 1; and (b) identifying the subject as positive for developing a thrombotic event if the molecular signature of the platelets include one or more molecular features of (a) an elevated phosphatidylserine level on the external surface of the platelets relative to a level of a control; (b) an elevated thrombin level on the external surface of the platelets relative to the level of the control; (c) an integrin GPIIb/IIIa activation level on the external surface of the platelets, wherein the level is not increased compared to the level of the control; (d) a glycoprotein GP Ib level on the external surface of the platelets, wherein the level is not increased compared to the level of the control; (e) a P-selectin level on the external surface of the platelets, wherein the level is not increased compared to the level of the control; (f) a decrease in platelet size relative to the platelet size of the control; (g) an increase in microparticle generation relative to the microparticle generation of the control, and (h) a change in membrane lipidomic profile compared to the membrane lipidomic profile of the control, preferably two or more features of (a)-(h), three of (a)-(h), at least four of (a)-(h), at least five of (a)-(h), at least six of (a)-(h), at least seven of (a)-(h), and all of (a)-(h).

C. Providing a Prevention and Management Regimen to a Subject

In some embodiments, the methods further include providing an appropriate therapy or protocol for the subject, for example, after reviewing the diagnostic results, to prevent or reduce the severity of an oncoming thrombotic event. In further embodiments, methods include treating a subject identified as positive for a thrombogenic status. The methods can reduce or prevent the onset or development of a thrombotic event, and/or treat, prevent or manage one or more thrombotic events in the subject relative to an untreated control subject.

The subjects of the disclosed methods can be an animal. The subjects are most typically mammals, for example humans.

Methods of treatment, method of monitoring treatment of a subject, and combinations are also provided. The methods of treatment can include monitoring the treatment, and any of the methods of monitoring can include treating the subject.

Typically, the methods of treatment include administered a subject a mechanoceutical in an effective amount to alter the molecular signature of platelets to one that reflects a less mechanically activated state. For example, the amount can be effective to reduce phosphatidylserine level on the external surfaces and/or reduce thrombin level on the external surfaces the subject's population of platelets; increase average platelet size in the subject's population of platelets; reduce microparticle generation in the subject's population of platelets; change the membrane lipidomic profile in the subject's population of platelets; or a combination thereof.

Methods for delivering an agent to a subject typically include administering to the subject one or more mechanoceuticals one or more times. The methods can also include creating a molecular signature of the platelets in the blood sample collected from the subject after administering the one or more mechanoceuticals. In some embodiments, the methods include creating a second, third, fourth, fifth molecular signature of the platelets in the blood sample collected from the subject later time points. The methods can include repeating the administration of the mechanoceutical if the level of phosphatidylserine, the level of thrombin, and/or the level of microparticle generation is reduced; the platelet size is increased; and/or the membrane lipidomic profile is changed; optionally the level of integrin GPIIb/IIIa activation and/or level of P-selectin in the platelets of the subject is not affected. In some embodiments, if the level of phosphatidylserine, the level of thrombin, and/or the level of microparticle generation is not reduced; the platelet size is not increased; and/or the membrane lipidomic profile is not changed; the dose, the frequency of administration of the mechanoceutical, or a combination thereof is increased, or a different mechanoceutical is administered to the subject. In some embodiments, the subject has a blood-contacting medical device implanted in the body prior to, contemporaneous with, simultaneous with, or after the first treatment with the mechanoceutical.

Methods of monitoring the prophylactic treatment of a subject are also provided. The methods can include, for example, creating a molecular signature of the platelets in the blood sample collected from a subject before treatment, treating the subject with a mechanoceutical one or more times, and creating a molecular signature of the platelets in the blood sample collected from the subject after treatment.

In some embodiments, treatment is repeated if the level of phosphatidylserine, the level of thrombin, and/or the level of microparticle generation is reduced; and/or the platelet size is increased; and/or the membrane lipidomic profile is changed; and/or optionally the level of integrin GPIIb/IIIa activation, the level of integrin GP Ib, and/or level of P-selectin in the platelets of the subject is not affected in the molecular signature of the platelets in the blood sample collected after from the subject after treatment relative to the molecular signature of the platelets in the blood sample collected from the subject before treatment. In some embodiments, if the level of phosphatidylserine, the level of thrombin, and/or the level of microparticle generation is not reduced; and/or the platelet size is not increased; and/or the membrane lipidomic profile is not changed in the blood sample collected from the subject after treatment relative to the molecular signature of the platelets in the blood sample collected from the subject before treatment the dose, the frequency of administration of the mechanoceutical, or a combination thereof is increased, or a different mechanoceutical is administered to the subject. In some embodiments, the methods include creating a third, fourth, fifth molecular signature of the platelets in the blood sample collected from the subject later time points, alone or in combination with one, two three, four, five, or more rounds of treatment at the same or different doses or frequencies of the same or a different mechanoccutical.

1. Conditions to be Treated

The basic function of platelets is to rapidly bind to damaged blood vessels, aggregate to form thrombi, and prevent excessive bleeding. However, activated platelets also aggregate at the site of atherosclerotic plaque ruptures and endothelial cell erosion, stimulating thrombus formation and promoting atherothrombotic disease. Thus, in some embodiments, the methods are used to detect early platelet activation and/or pre-diagnose thrombotic events in a subject at risk of developing one or more thrombotic diseases.

In some embodiments, the subject to be treated is one with a blood-contacting device, such as mechanical circulatory support devices and ventricular assist devices (VADs).

Venous thromboembolism (VTE) is a common complication in patients with malignant disease. Emerging data have enhanced the understanding of cancer-associated thrombosis, a major cause of morbidity and mortality in patients with cancer. In addition to VTE, arterial occlusion with stroke and anginal symptoms is relatively common among cancer patients, and is possibly related to genetic predisposition. Several risk factors for developing venous thrombosis usually coexist in cancer patients including surgery, hospital admissions and immobilization, the presence of an indwelling central catheter, chemotherapy, use of erythropoiesis-stimulating agents (ESAs) and new molecular-targeted therapies such as antiangiogenic agents. In some embodiments, the methods are used in a subject with a proliferative disease, e.g., cancer, especially those at risk of developing cancer-associated thrombosis Inflammation shifts the hemostatic mechanisms in favor of thrombosis. In some embodiments, the methods disclosed herein are for use in a subject with inflammation, especially those with increased thrombotic tendency. Exemplary systemic inflammatory diseases characterized by thrombotic tendency, including but not limited to Behçet disease (BD), antineutrophilic cytoplasmic antibody-associated vasculitides, Takayasu arteritis, rheumatoid arthritis, systemic lupus erythematosus, antiphosholipid syndrome, familial Mediterranean fever, thromboangiitis obliterans (TAO) and inflammatory bowel diseases.

2. Mechanoceuticals

One or more mechanoceuticals can be administered to modify properties of the surface of the platelets. For example, the mechanoceuticals can be administered in an effective amount to reduce membrane rigidity/stiffness and/or increase membrane fluidity of platelets in the blood. Increasing membrane fluidity of platelets is effective to "rubberize" the membrane, allowing it to tolerate more exogenous physical force and/or shear, effectively desensitizing it to these stimuli.

Compositions can be administered which include one or more mechanoceuticals useful for the modulation of cellular processes that contribute to onset and progression of thrombosis. In some embodiments, the compositions contain an effective amount of the mechanoceutical(s) to reduce the number of mechanically-activated platelets in the blood. In some embodiments, the compositions contain an effective amount of the mechanoceutical(s) to reduce membrane rigidity/stiffness and/or increase membrane fluidity of platelets in the blood.

Methods of measuring membrane stiffness have been described, for example using Dielectrophoresis (DEP) and electro-deformation (EDF), in which platelets are gently stretched by oscillating (alternating) electrical fields, which deform the platelet and provide a measure of its stiffness without inducing activation (Leung S L et al., Ann Biomed Eng. 44(4): 903-13 (2016)). In some embodiments, the compositions are effective to reduce membrane rigidity/stiffness of platelets to be lower than 5 kPa, lower than 3.5 kPa, or lower than 3.0 kPa.

i. Exemplary Mechanoceuticals

A variety of mechanoceuticals and methods for administering the mechanoceuticals are described in WO 2015/113001 to Marvin Slepian. Preferred agents are lipids and lipid related compounds. Lipids may be broadly defined as hydrophobic or amphiphilic small molecules; the amphiphilic nature of some lipids allows them to form structures such as vesicles, multilamellar/unilamellar liposomes, or membranes in an aqueous environment. Useful lipids include fatty acids, glycerolipids, glycerophospholipids, sphingolipids, saccharolipids, and polyketides (derived from condensation of ketoacyl subunits); and sterol lipids and prenol lipids (derived from condensation of isoprene subunits).

Agents that are capable of modulating membrane fluidity include but are not limited to, dimethysulfoxide (DMSO), gangliosides, interpolating lipids, hormones, or sterols, cholestrol, cholesterol hemisuccinate, lidocaine, procaine, sex steroids, phenytoin, Docohexanoic acid, cortisol, estradiol, PGE2, progesterone, medroxyprogesterone, insulin, glucagon, atropine, carbachol, lutropin, neuropeptide Y, thyroid hormone, aldosterone, vasopressin, perylene, 9-(dicyanovinyl) julodinine, 1,6-diphenyl-1,3,5-hexatiene (DPH), TMA-DPH, DPH-PA, cis and trans-parinaric acid, polyunsaturated fatty acids, phospatidyl choline, phospahtidylserine, phospatidyl inositol, insitol, choline, cerebroside, glycoshpingolipids, and sphingomyelin, and combinations thereof.

The mechanoceuticals can be administered alone, or in combination with other agents such as a polymeric coating, agents that alter submembrane assemblies, modulate intracellular microfilament or microtubule function or agents that modulate intracellular fluid content and tonicity. In a preferred embodiment, the cholesterol administered is non-atherogenic. Agents that can alter sub-membrane assemblies involved in mechano-transduction include, but are not limited to NSAIDs, e.g. sulindac sulfide, and phenolic antioxidants, caffeic acid phenethyl ester (CAPE), which may modulate Focal Adhesion Kinase (FAK, also known as PTK2 protein tyrosine kinase 2 (PTK2)) signaling. Weyant, et al., "Colon cancer chemoprotective drugs modulate integrin-mediated signaling pathways", Clin Cancer Res, 6:949 (2000). Similarly, resveratrol may modulate FAK as well.

Rho kinase inhibitors, e.g. Y-27632 including FAK, talin and other linkage and phosphorylated proteins, may be included in the compositions in an effective amount to limit shear-mediated platelet activation, and administered to the cells.

Additional useful agents include, but are not limited to, phenolic antioxidants, caffeic acid phenethyl ester (CAPE) FAK signaling and modulating agents, resveratrol, Rho kinase inhibitors, e.g. Y-27632, inhibitors or modulators of talin, paxillin, and vinculin and similar submembrane mechnotrasnductive proteins.

Agents that can modulate intracellular microfilament function can be administered in an effective amount to increase the microfilament assembly and/or integrity. Suitable agents that are capable of modulating intracellular microfilament function include, but are not limited to, cytochalasins (e.g. cytochalasin B), concanavalin, vincristine, vinblastine, oryzalin, trifluralin, taxol, taxetere and similar compounds.

Agents that can modulate intracellular microtubule function can be administered in an effective amount to increase the microtubule assembly and/or integrity. Suitable agents that are capable of modulating intracellular microtubule function include, but are not limited to colchicine, colcemid, vinblastine, vincristine, taxol, taxetere, 9-bromonscapine (EM011), docetaxel, noscapinoids, and tau.

Optionally, the mechanoceutical compositions include one or more agents in an effective amount to modulate intracellular fluid content and tonicity. For example, the compositions may include hypo or hypertonic solutions, for example, saline, lactated ringers, dextrose, sucrose, mannitol, or similar small molecules.

In these embodiments, the cells may be contacted (in vivo) with or incubated ex vivo in hypo or hypertonic solution. The cells may also be contacted with aquaporin receptors modulating agents, agonists or antagonists, Hg Cl2, G-protein modulating agents, vasopressin receptors modulators, including V1a, V1b and V2, tolvaptan, conivaptan, and/or other vaptans.

ii. Methods of Administering the Mechanoceuticals

The mechanoceuticals can be included in a composition, along with a suitable carrier.

The compositions may be administered by a variety of suitable methods, including, but not limited to, orally, systemically, locally, regionally, enterally, parenterally, and subcutaneously. For example, a catheter can be inserted into a patient, and the composition can be infused, perfused, or superfused to the desired site to expose the cells thereto. For regional delivery, the composition may be administered via an osmotic pump.

D. Methods of Selecting a Medical Device

Methods for selecting a blood-contact medical device for implanting into a subject in need thereof are provided.

Exemplary blood-contact medical devices include mechanical circulatory support device, ventricular assist devices (VADs). Various long-term implantable ventricular assist devices are commercially available including those using Axial Flow (e.g., HEARTMATE II® by Thoratec, HEART ASSIST 5® by Reliant Heart, JARVIK 2000® by Jarvik Inc), using Centrifugal Flow (e.g., HVAD® by Heart-Ware, DURAHEART® by Terumo, HEARTMATE III® by Thoratec), using mixed flow (e.g., SYNERGY® by Circu-Lite, and MVAD® by HeartWare), and using flower maker (e.g., INCOR® by Berlin Heart). Methods for selecting a mechanical circulatory support device with optimal benefits and minimal risks of device-related adverse events such as thrombosis in a subject are described.

Typically, ex vivo methods for selecting a blood-contacting medical device for implanting into a subject in need thereof include the steps of (i) modeling a shear stress profile of a blood-contacting medical device; (ii) reproducing the shear stress profile of blood flow in a microfluidic device; (iii) flowing a sample containing platelets collected from a subject through the microfluidic device; (iv) creating a molecular signature of the platelets by measuring a composite of at least two of (a) phosphatidylserine, (b) thrombin, (c) integrin GPIIb/IIIa, (d) glycoprotein GP Ib, (e) P-selectin; (f) platelet size; (g) microparticle generation, and (h) lipidomic profile of the membrane, preferably at least three of (a)-(h), at least four of (a)-(h), at least five of (a)-(h), at least six of (a)-(h), at least seven of (a)-(h), and all of (a)-(h). Typically, the device for modeling a mechanical stimulus emulates thrombogenicity, produces a probability density function of the blood-contacting medical device, and determines trajectories for individual particles flowing through the blood-contacting medical device.

The methods further involves the step of selecting a blood-contacting medical device if one or more of the level of phosphatidylserine, the level of thrombin, and the level of microparticle generation is lower than the levels in the molecular signature of mechanically activated platelets, if the platelet size is greater than the platelet size in the molecular signature of mechanically activated platelets; or a combination thereof; optionally the level of integrin GPIIb/IIIa, the level of integrin GP Ib, and/or the level of P-selectin in the platelets of the subject is not different than each of these in the mechanically activated platelets.

In some embodiments, the methods involve creating a molecular signature of two, three, four, five or more blood-contacting medical devices. The methods further include the step of selecting a device with the lowest level of phosphatidylserine on the external surface of the platelets, the lowest level of thrombin on the external surface of the platelets, and/or the lowest level of microparticle generation for implant into the subject in need thereof.

E. Methods of Screening Mechanoceuticals

Routine clinical anti-platelet agents have limited efficacy in modulating hypershear-mediated platelet activation associated with mechanical circulatory support (Valerio L et al., Thromb Res. 163:162-171 (2018)). Thus, methods for screening mechanoceuticals suitable for modulating hypershear-mediated platelet activation associated with mechanical circulatory support are provided.

Generally, screening mechanoceuticals under a mechanical stimulus similar to that in a subject at risk of developing a thrombotic even is desirable, for example in a microfluid device modeled with the shear stress profile of a subject at risk of developing a thrombotic event. Similar microfluidic devices have been described previously, for example in U.S. Publication No. 2017/0246632, and by Dimasi A et al. (Dimasi A et al., Med Eng Phys. 48:31-38 (2017)).

Methods of selecting a mechanoceutical agent are also provided. The methods can include, for example, reproducing a mechanical stimulus profile of blood flow in a microfluidic device; flowing a sample collected from the subject through the microfluidic device in the presence and absence of a test agent, wherein the sample comprises platelets separated from a blood sample obtained from a subject;

creating a molecular signature of the platelets in the presence and absence of the test agent; and selecting the test agent as a mechanoceutical if the level of phosphatidylserine on the external surface of platelets, the level of thrombin on the external surface of platelets, and/or the level of microparticle generation is lower in the presence of the test agent than in the absence of the test agent.

F. Controls

The effect of mechanically activated platelets can be compared to a control. For example, in some embodiments, the control cells are platelets directly healthy subjects with minimal risk of developing thrombosis.

One of skill can identify a suitable control or standard for use the methods disclosed herein. For example, in some embodiments, the control is a molecular signature of a population of resting platelets, preferably prepared in the same or similar manner as the signature of the test platelets subject to the disclosed methods. In some embodiments, the control molecular signature is prepared in parallel with the test signature. In other embodiments, the control molecular signature is prepared at a different time from the test signature. Thus, in some embodiments, the control is a reference signature or indices otherwise associated with non-mechanically active platelets. The platelets utilized for the control signature can be, but need not be, derived or collected from the blood of the same subject as the platelets utilized for the test signature. For example, in some embodiments, the control platelets are collected from any individual who has not had a medical device (e.g., a blood-contacting medical device) implanted therein. In some embodiments, the control platelets are collected an individual before undergoing an implantation procedure (e.g., of an implantation of a blood-contacting medical device), and test platelets are collected from the same individual after undergoing the implantation procedure.

The effect of a mechaniceutical agent can be compared to a control. For example, in some embodiments, one or more of the pharmacological or physiological markers or pathways affected by mechaniceutical agent treatment is compared to the same pharmacological or physiological marker or pathway in untreated control cells or untreated control subjects. For example, cell surface markers of platelets including phosphatidylserine, thrombin, GP Ib, integrin GPIIb/IIIa activation, P-selectin are measured in mechaniceutical agent treated cells or subjects and compared to untreated cells or subjects. In some embodiments, an untreated control is derived from the same source as the treated sample, for example, cells isolated from a patient at a risk of developing a thrombotic event. In some embodiments, the untreated cells are platelets with a cardiovascular pathology having the molecular signature of mechanically activated platelets.

The present invention will be further understood by reference to the following non-limiting examples.

EXAMPLES

Example 1: Platelet P-Selectin Exposure Occurs after a Stimulation with Biochemical Activators but not Uniform Continuous Shear Stress Methods Blood Collection and Platelet Fraction Isolation.

All healthy volunteers gave their written informed consent and claimed not to have taken antiplatelet medications two weeks prior to blood draw. The study protocol was approved by the Institutional Review Board at the University of Arizona concerning human subjects. Blood was drawn from forearm by venipuncture via 21-gauge (0.8×19 mm) butterfly needle into 30 mL syringe and transported in polypropylene conical tube containing 3 mL of acid citrate dextrose anticoagulant solution (107 mM trisodium citrate, 60 mM citric acid, 199 mM glucose). Platelet-rich plasma (PRP) was obtained by centrifugation of anticoagulated blood at 400 g for 15 minutes at room temperature with no brake applied. PRP, as a supernatant, was collected and placed into a new tube with a plastic transfer pipette. To get platelet-poor plasma (PPP) the remaining blood was centrifuged at 1430 g for 20 minutes at room temperature. Gel-filtered platelets (GFP) were isolated after PRP filtration through Sepharose 2B column (35×250 mm) equilibrated with HEPES buffer (10 mM HEPES, pH-7.4, 125 mM NaCl, 2.7 mM KCl, 2 mM MgCl, 0.5 mM $NaH_2PO_4$, 1 mM trisodium citrate, 25 mM glucose and 0.1% BSA). Platelet count was quantified with Z1 Coulter Particle Counter (Beckman Coulter Inc., Indianapolis, IN). Platelet fractions were stored and handled at room temperature if not otherwise indicated.

Platelet Aggregation Induced with Biochemical Agonists

Platelet aggregation was assessed in PRP or GFP samples employing dual channel optical aggregometer (Model 560-VS, Chrono-Log Corporation, Havertown, PA). 10 uM ADP (Sigma-Aldrich, St. Louis, MO), 10 µg/mL epinephrine (Sigma-Aldrich, St. Louis, MO), 32 µM TRAP6 (Roche Diagnostics GmbH, Mannheim, Germany), 1 U/mL thrombin (Sigma-Aldrich, St. Louis, MO), 100 µg/mL collagen (MP Biomedicals, Solon, OH) or 1 mM arachidonic acid (BioData, Horsham, PA) were utilized to induce platelet aggregation response. Platelet count in aggregation mixture was adjusted to 150-200×10³ plt/µL (in GFP) and to 300-350×10³ plt/µL (in PRP), final CaCl2 concentration was 1 mM. Aggregation was started by adding mentioned agonists and running for 5 minutes at 37° C. with 1000 rpm stirring. The changes in relative light transmittance were recorded, and arbitrary values for each aggregation curve were calculated with Aggrolink software (Chrono-Log Corporation, Havertown, PA).

Shear-Mediated Platelet Activation

Platelets were exposed to uniform continuous shear stress in the hemodynamic shearing device (HSD), a computer-controlled cone-plate-Couette viscometer, specifically designed to generate precisely controlled and uniformly distributed shear stress to all platelets in the flow field (Nobili et al., ASAIO J. (*American Soc. Artif. Intern. Organs*), vol. 54, no. 1, pp. 64-72, (2008)). GFP were diluted with HEPES buffer to final platelet count 2×10⁴ platelets/µL, and CaCl2 (2.5 mM) was added 3 min prior to HSD run. Constant shear stress modes of three magnitudes (30, 50 and 70 dynes/cm²) were utilized. Samples for flow cytometry and platelet activation state (PAS) assay were taken from the annular region of the HSD at 0 and 10 minutes time points.

To emulate dynamic shear pattern found within MCS conditions, an in vitro VAD-employed loop system was built using axial continuous flow VAD HeartAssist 5 (MicroMed Technology Inc., USA) and ½" diameter non-thrombogenic tubing. Outflow graft-aorta anastomotic angle of 90 degrees was emulated by insertion of angulated connector. GFP (2×10⁴ platelets/µL, 2.5 mM CaCl₂)) were circulated through the VAD loop system at 8000 rpm at room temperature, samples were collected at 0, 2, 5, 10, 30, and 60 minutes time points, and processed immediately.

To establish a positive control for SMPA and a reference maximum for annexin V binding and PAS values, fully activated platelets were obtained by sonication (10 W for 10 s, Branson Sonifier 150 with microprobe, Branson, MO, USA) (Schulz-Heik et al., *Pathophysiol Haemost. Thromb.*, vol. 34, no. 6, pp. 255-262, June (2006)). Sonication mixture (350 µL) contained $2 \times 10^4$ platelets/µL and 2.5 mM $CaCl_2$). Flow Cytometry Detection of Platelet Activation State Markers To induce biochemical activation, GFP ($2 \times 10^4$ platelets/µL, final volume 100 µL) were treated with biochemical agonists mentioned above in presence of 2.5 mM $CaCl_2$), mixed gently and incubated undisturbed for 15 minutes at room temperature. Then APC-conjugated anti-CD62P (clone Psel.KO2.3, eBioscience, San Diego, CA) and FITC-labeled annexin V (eBioscience, San Diego, CA) were added to indicate platelet a-granule secretion and phosphatidylserine externalization (PSE) during platelet biochemical activation. Integrin GP αIIbβ3 activation was evaluated by double-staining technique. APC-conjugated anti-CD41 (clone MEM-06, Thermo Scientific, Rockford, IL) bound to integrin subunit αIIb presented on the surface of both intact and activated platelets. FITC-anti-CD41/CD61 (clone PAC-1, BioLegend, San Diego, CA) bound to activation-induced conformational epitope of the integrin αIIbβ3 and mark only activated platelets. A pair of antibodies against αIIbβ3 was added simultaneously into a test tube containing activated platelet sample to identify the number of platelets exposing activated αIIbβ3 among all αIIbβ3-expressing platelet population. Cells were incubated with annexin V or antibodies for 30 minutes at room temperature in the dark, washed by centrifugation (5000 rpm, 5 min), resuspended in 1 ml of Ca-free 0.05 M phosphate buffer (pH-7.4) and transferred in polystyrene tube for flow cytometry. Flow cytometry analysis was performed within 15 minutes after sample preparation.

Shear-stimulated and sonicated platelet samples were incubated with annexin V or fluorophore-labeled antibodies immediately after HSD run or sonication procedure. To avoid time-dependent fluorescence signal dissipation, those samples were fixed with 3.5% PFA in PBS for 20 minutes at room temperature, washed and resuspended in PBS as described above for biochemically activated platelets.

Flow cytometry was performed on FACS Canto II (BD Biosciences, San Jose, CA) using the following configurations: HeNe red laser (633 nm) and 660/20 filter—for APC, solid state blue laser (488 nm) and 530/30 filter—for FITC-stained cell detection. Single platelets were distinguished from their aggregates and microparticles based on their characteristic forward versus side scatter. Percentage of activation was quantified as the fraction of platelets that displayed greater than baseline levels of annexin V binding and platelet activation state markers. BD FACSDiva™ software was applied to analyze flow cytometry data statistics (percentage of marker-positive platelets among whole platelet population and their median fluorescence intensity). Statistical Analysis Flow cytometry and PAS assay samples were run in two repetitions; results from four to six independent experiments with different donors were summarized in plots. The data were statistically analyzed using one-way analysis of variance (ANOVA) from Microsoft Excel software package (Microsoft, Redmond, WA). Averages are reported as the mean±margin of error. The level of statistical significance is indicated in the figures as $p < 0.05$ (*) and $p < 0.01$ (**). Results To define the molecular signature of SMPA, biochemical versus mechanical platelet activation by uniform shear stress applied in the hemodynamic shearing device (HSD) was compared. To induce biochemical activation, human GFP were treated with the panel of physiologically relevant soluble agonists-ADP, epinephrine, TRAP-6, thrombin, collagen or arachidonic acid. Agonists' effective concentrations were chosen considering their ability to induce platelet aggregation in GFP (TRAP-6, collagen, arachidonic acid, and thrombin) and/or PRP (ADP, epinephrine) (FIGS. 1A-1F). Mechanical platelet activation was obtained via GFP exposure to uniform continuous shear in HSD as described above in "Shear-mediated platelet activation". Physiologically relevant shear stress levels (30 and 50 dynes/cm²) close to those found in blood stream vs. sub-pathological shear conditions (70 dynes/cm²) existing within MCS were examined. Initially, the P-selectin exposure, as a known marker of platelet activation and α-granule secretion, was detected employing mono immunostaining and quantified by flow cytometry. Those cells showing high fluorescence intensity (≥3000 AU) were gated as P-selectin positive platelets and marked as sub-population P6 (FIGS. 2A-2G).

It was observed that all biochemical agonists induced P-selectin exposure, but the extent of their action was notably differed. In FIGS. 2A-2G, the significant shift of fluorescence intensity peak to the right side after platelet biochemical activation is present indicating the intensification of P-selectin exposure on the surface of biochemically activated platelets. "Weak" agonists, epinephrine (FIG. 2C) and ADP (FIG. 2B), induced modest P-selectin exposure, the number of CD62P-positive cells was 18.6±1.5% and 46.8±3.9% of whole platelet population, respectively. After arachidonic acid stimulation, 52.1±6.8% of cells presented P-selectin (FIG. 2G); TRAP-6 and thrombin promoted the dramatic augmentation of P-selectin exposure (FIG. 2E), A clear majority of platelets bared the protein marker on their surface. Among "strong" agonists, only collagen failed to induce high P-selectin exposure under experimental conditions employed (FIG. 2D).

The median fluorescence intensity of CD62P-positive platelets grew at the same manner as their number in each experimental group of cells treated with biochemical agonists (data not shown).

Platelets subjected to all levels of uniform shear expressed low levels of P selectin on their surface (FIGS. 3A-3F). As compared with intact platelets, the number of CD62P-positive platelets was not significantly increased after physiologically relevant shear (FIGS. 3A-3B, groups "Intact platelets" vs. "30 dynes/cm²") and was approximately three times as high after platelet exposure to relatively high shear stress, achieving 15.5±3.6% and 18.8±4.2% after 50 and 70 dynes/cm², respectively. Likewise, fluorescence intensity levels were barely increased (data not shown). Sonicated platelets, established as a positive control for mechanical platelet activation (Schulz-Heik et al., *Pathophysiol. Haemost. Thromb.*, vol. 34, no. 6, pp. 255-262, June (2006)), also showed low level of P-selectin appeared on their surface. Neither CD62P-positive platelet number nor their fluorescence intensity were notably elevated as a result of platelet sonication in presence of 2.5 mM $CaCl_2$).

Figures 4A, 4B, 4C, 4D, 4E:
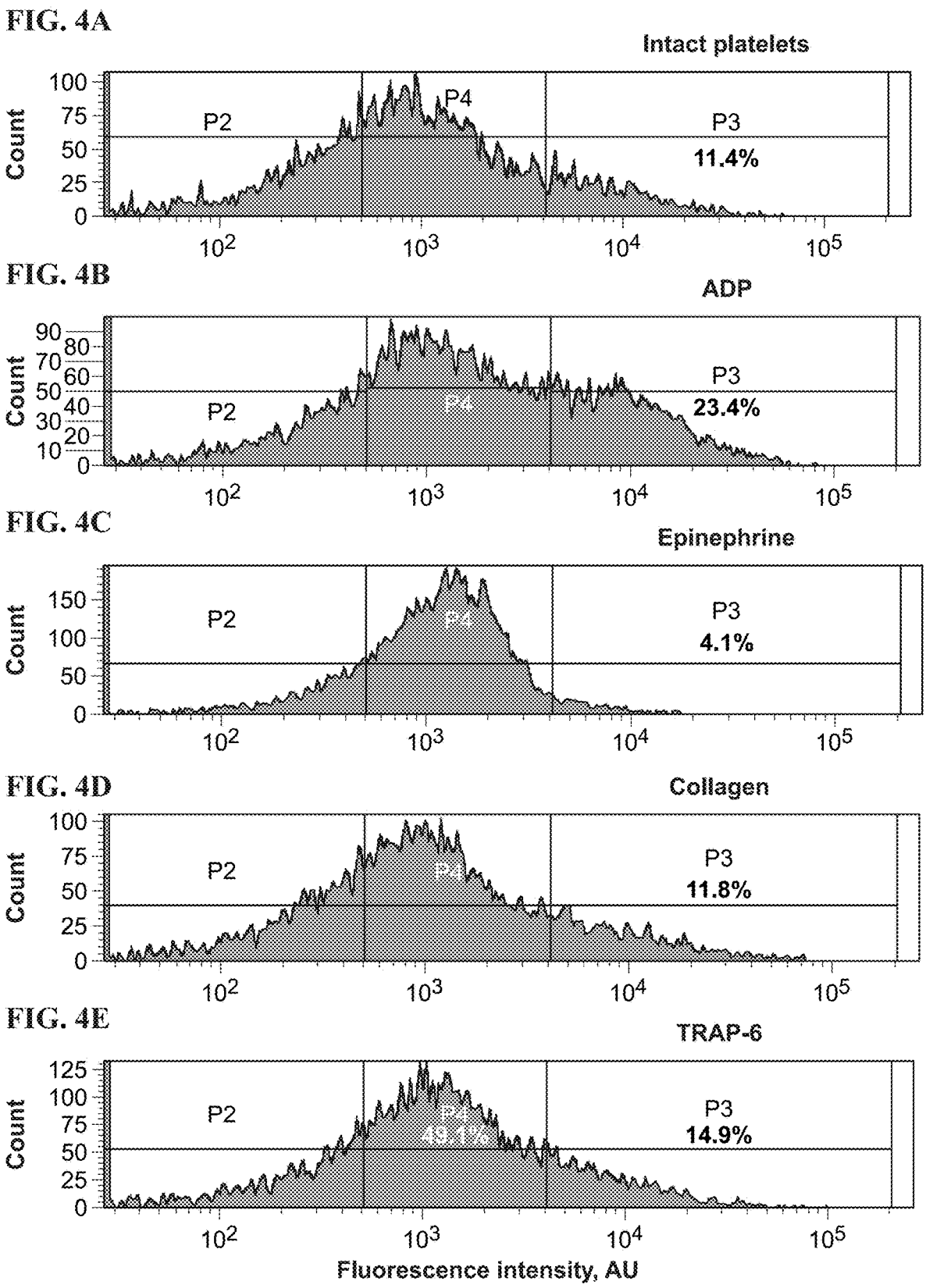

Example 2: Platelet Integrin GPIIb/IIIa Activation by Biochemical Agonists Versus its Downregulation after Continuous Shear Stress Results To assess the magnitude of integrin GPIIb/IIIa activation after platelet stimulation with constant shear or biochemical agonists, the number of whole GPIIb/IIIa-positive platelet population was compared with the number of those presenting activated form of the integrin on their membrane. For this purpose, double staining with APC-conjugated anti-CD41 and FITC-conjugated anti-CD41/CD61 was applied as describe in the methods described above. Among parental CD41-positive platelet population, CD41/CD61-positive cells were distinguished based on their FITC-fluorescence intensity level (≥4000 AU) and assumed as presenting activated form of integrin GPIIb/IIIa on their surface (FIGS. 4A-4G, sub-population P3). The increase of fluorescence intensity, as a significant right-side shift of fluorescence peak, was notable only after ADP and thrombin stimulation of GFP. As shown on FIGS. 4B and 4F, the number of platelets presenting activated GPIIb/IIIa in ADP- and thrombin-treated cell groups was elevated correspondingly in 4.2 and 9.6 times as compared with intact platelets (28.0±8.9% and 63.5±10.2% vs. 6.7±2.9%). Surprisingly, other biochemical activators failed to promote GPIIb/IIIa activation: the number of CD41/CD61-positive platelets was not significantly elevated following GFP stimulation by epinephrine (FIG. 4C), collagen (FIG. 4D), TRAP-6 (FIG. 4E), or arachidonic acid (FIG. 4G).

Figures 5A, 5B, 5C, 5D, 5E:
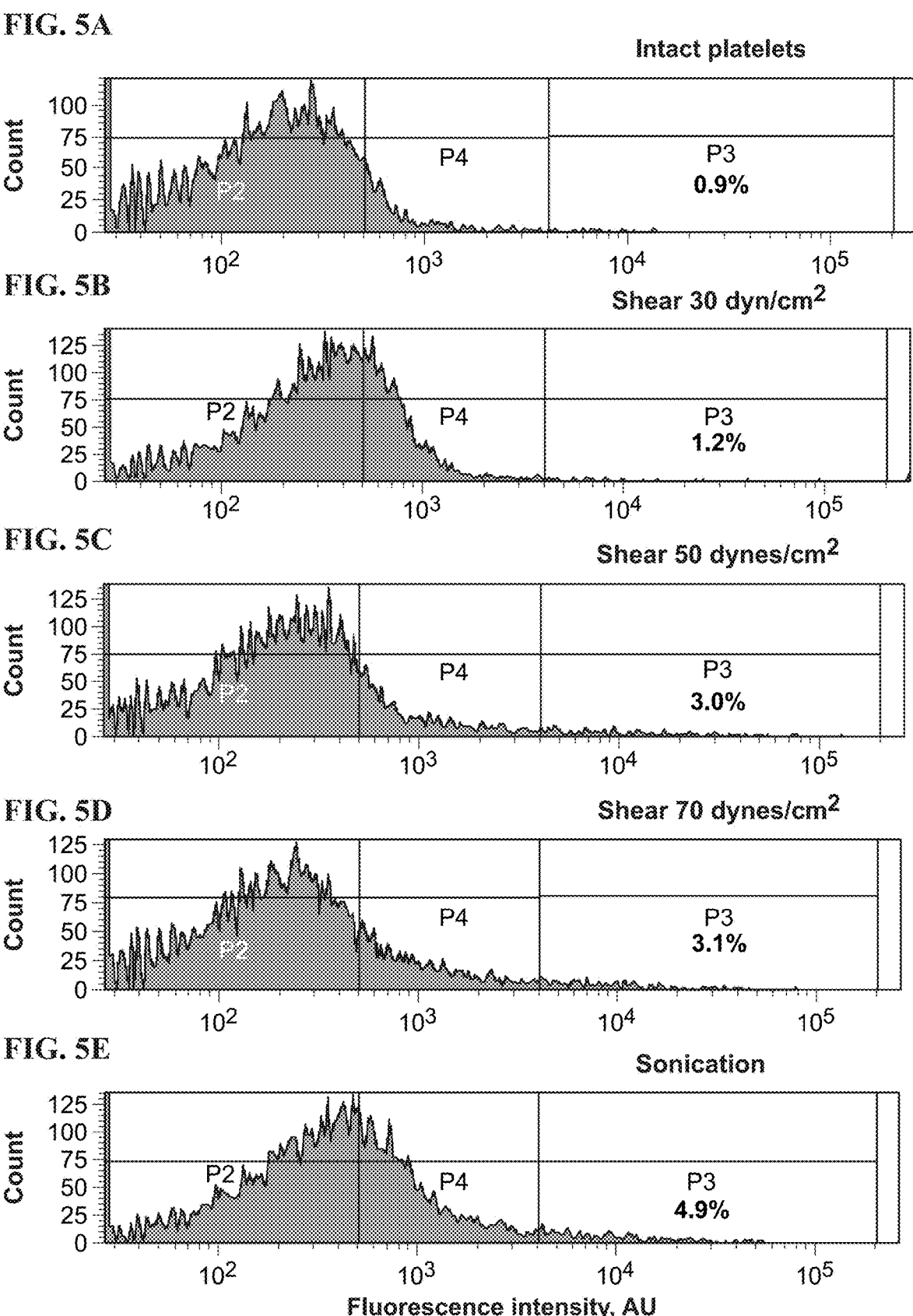
FIGS. 5A-5F are graphs showing human platelet integrin GPIIb/IIIa-activation induced by constant uniform shear.
Figure 5F:
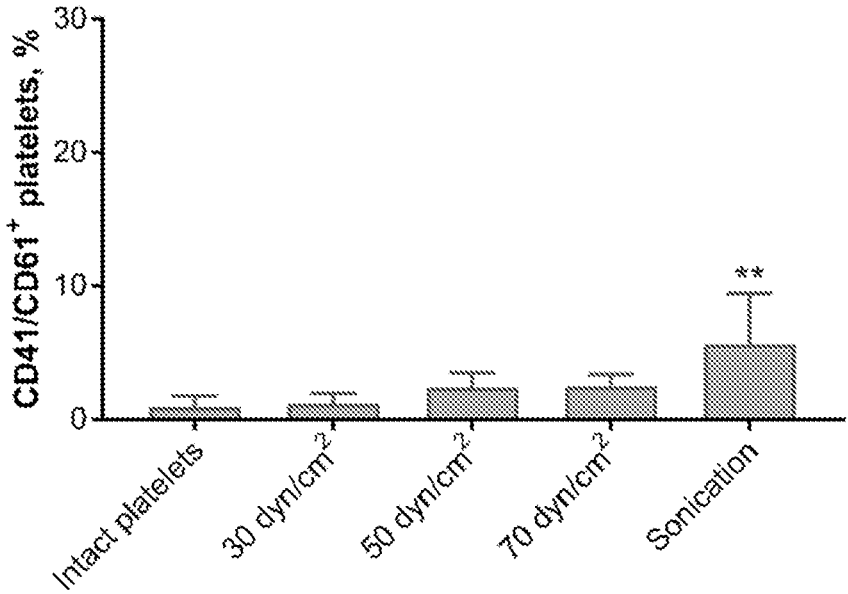

Strikingly, platelet exposure to uniform continuous shear stress did not promote integrin GPIIb/IIIa activation: the number of platelets presenting activated form of GPIIb/IIIa was not increased after 30, 50 or 70 dynes/cm$^2$ shear stress levels were applied. Similarly, in the sonicated platelet sample only 5.6±3.3% of cells expressed activated GPIIb/IIIa on their surface (FIGS. 5A-5F). Moreover, it was observed that platelet exposure to high shear led to down-regulation of GPIIb/IIIa surface expression. As such, the number of GPIIb/IIIa-positive platelets in GFP subjected to sub-pathological shear (70 dynes/cm$^2$) was minimally but statistically significantly decreased (88.0±2.4% vs. 93.8±1.3% in "Intact platelets", FIG. 5D). Sonication resulted in further deprivation of CD41-positive platelet count down to 81.8±3.3% (FIG. 5E). Following the same tendency, the fluorescence intensity of CD41-positive platelets was also decreased by 1.4 and 1.8 times after 70 dyn/cm$^2$ shear stress and sonication, respectively, as compared with intact platelets (FIG. 5C).

It was found that after SMPA, the forward scatter (FCS-A) of CD41-positive platelets, an indicator of their size, was distinctly decreased as shear force magnitude increased (FIG. 6C), and the extent of FCS-A reduction was comparable to fluorescence signal dissipation.

Example 3: Phosphatidylserine Externalization and Thrombin Generation on Platelet Surface as a Result of Shear-Mediated but not Biochemical Activation Methods Platelet Activation State (PAS) Assay PAS was quantified by chemically modified prothrombinase-based chromogenic assay developed by Jesty and Bluestein (Jesty & Bluestein, *Anal. Biochem.* (1999), Jesty et al., *Platelets*, vol. 14, no. 3, pp. 143-149, 2003). The assay measures the rate of acetylated thrombin generation from acetylated proenzyme cleavage by factor Xa in presence of activated platelets. Unlike native enzyme, acetylated thrombin possesses amidolytic activity on peptide substrate but is not capable to activate platelets in a feedback manner. Activated, but not resting, platelets present factor Va and negatively charged phospholipids (mostly phosphatidylserine) on their surface for prothrombinase complex formation and thrombin generation. Thus, the rate of enzymatic cleavage of chromogenic substrate Chromozym TH (Tosyl-Gly- Pro-Arg-4-nitranilide acetate, Roche Diagnostics GmbH, Mannheim, Germany) by acetylated thrombin reflects the value of initial activation state of the platelets tested (Jesty & Bluestein, *Anal. Biochem.* (1999), Rubenstein et al., *Circulation*, (2004)).

Platelet samples preliminary stimulated with biochemical activators, shear or sonication (platelet count—5×10$^3$ cells/μL) were incubated with 200 nM acetylated prothrombin, 100 pM factor Xa (Enzyme Research Laboratories, South Bend, IN), 5 mM CaCl$_2$) in a volume of 100 μL 20 mM HEPES, pH 7.4, containing 130 mM NaCl and 0.1% BSA at 37° C. for 10 minutes. Then, 10 μL of each timed sample was measured for thrombin activity in microplate wells, containing 0.3 mM Cromozyme TH, 3 mM EDTA in 20 mM HEPES, pH 7.4, containing 130 mM NaCl and 0.1% BSA. Kinetic change of absorbance (λ=405 nm) was measured for 7 minutes at room temperature using microplate reader Versa MAX (Molecular Devices Corp., Sunnyvale, CA). The value of PAS or initial rate of thrombin generation was calculated as a slope of kinetic curve (ΔA405/min) with SoftMax Pro6 Software.

Results

Figure 7A:
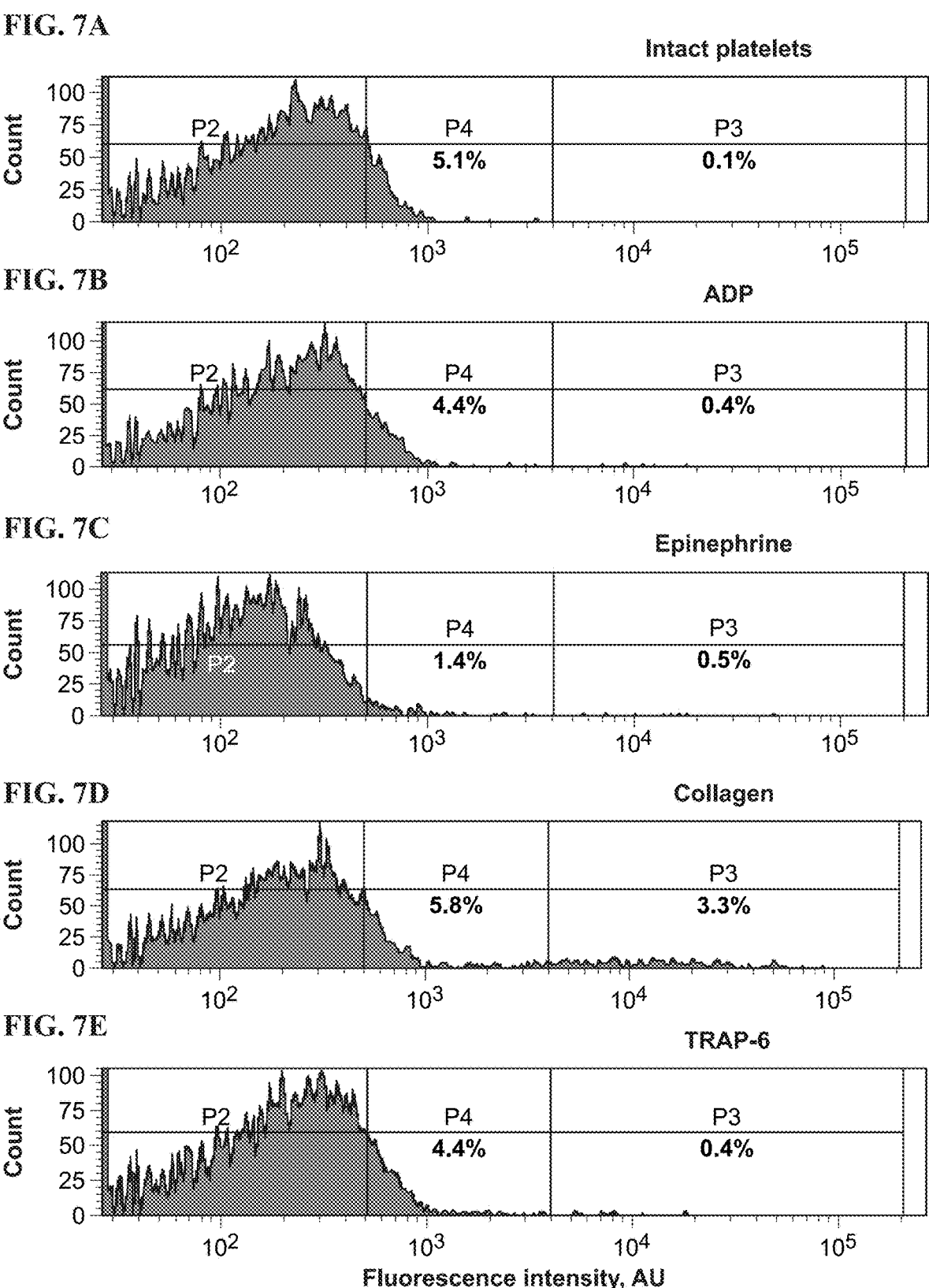

To detect phosphatidylserine exposure, an annexin V binding assay is extensively utilized. The principle of the assay is based on the high affinity binding of protein annexin V labeled with fluorescence dye to phosphatidylserine on platelet surface with the aid of Ca2+ ions (Demchenko, *Cytotechnology*, vol. 65, no. 2, pp. 157-72, March (2013)). In this study, annexin V binding was measured to define the capability of biochemical agonists vs. shear stress to induce platelet PSE and hence procoagulant activity. No annexin V binding was observed after platelet stimulation with ADP, epinephrine, collagen, TRAP-6, or thrombin taken alone (FIGS. 7A-7H), even though they induced aggregation, integrin GPIIb/IIIa activation and/or P-selectin exposure. Arachidonic acid (1 mM) was the only biochemical agonist shown to promote significant annexin V binding: the number of annexin V-positive platelets reached 52.12±6.79% of whole platelet population (FIG. 7G).

Figures 8A, 8B, 8C, 8D, 8E:
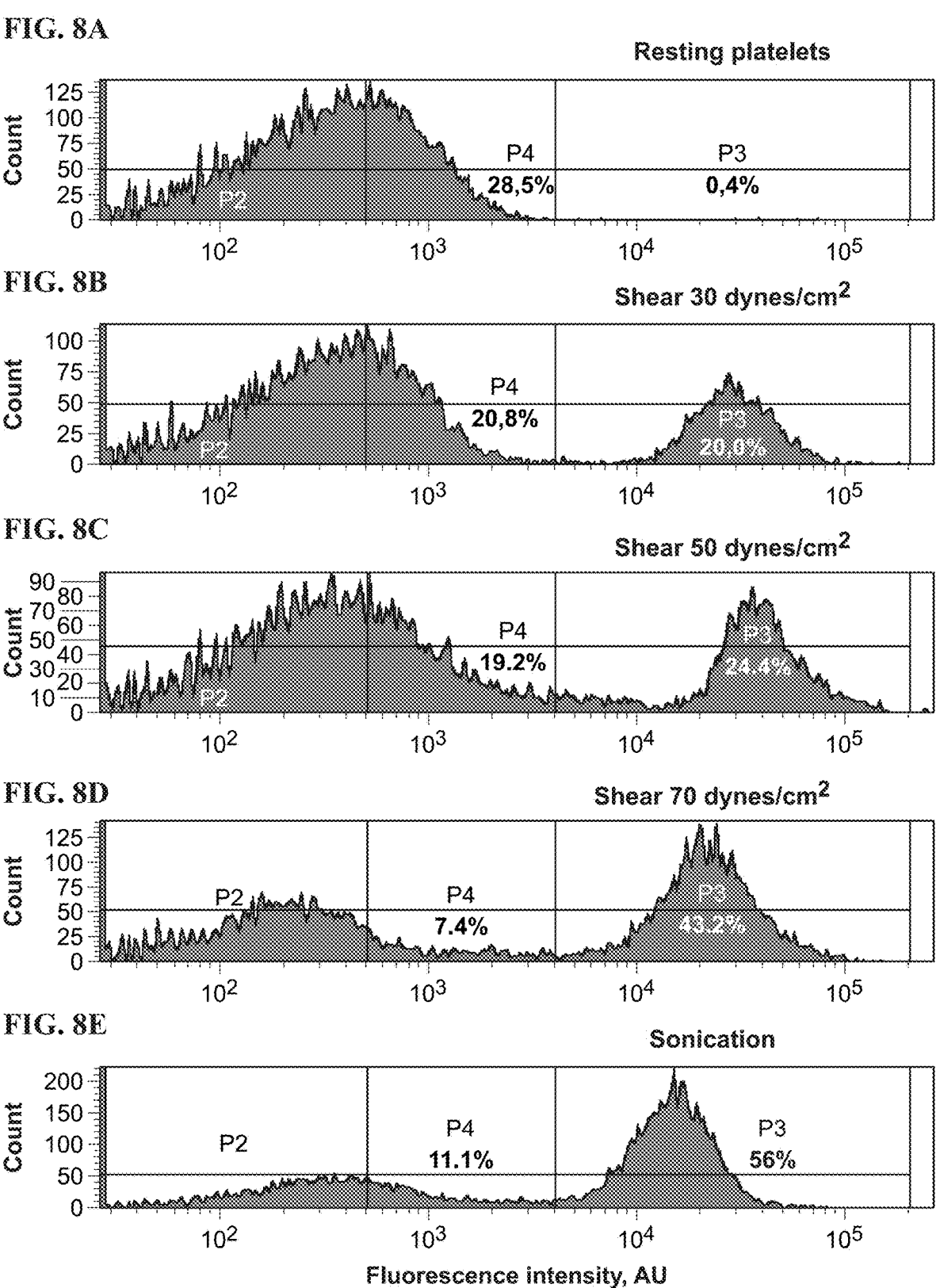
FIGS. 8A-8G are graphs showing human platelet phosphatidylserine externalization induced by constant uniform shear.
Figure 8F:
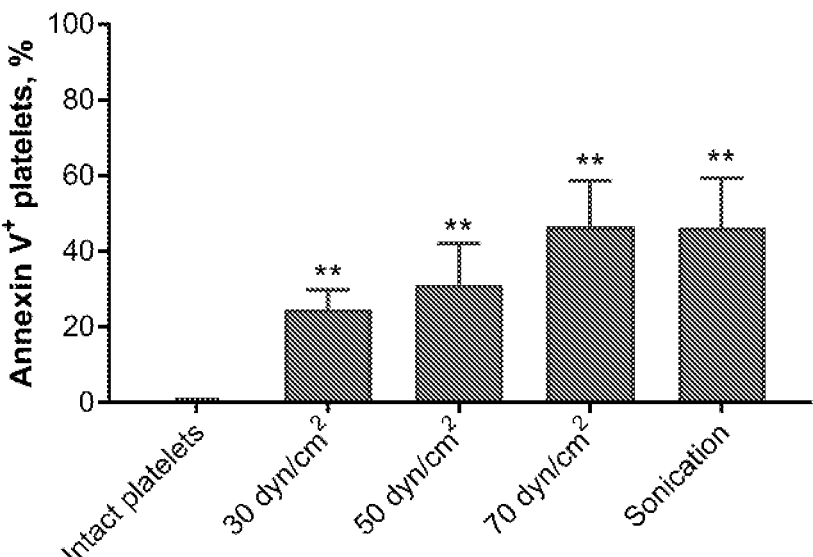
Figure 8G:
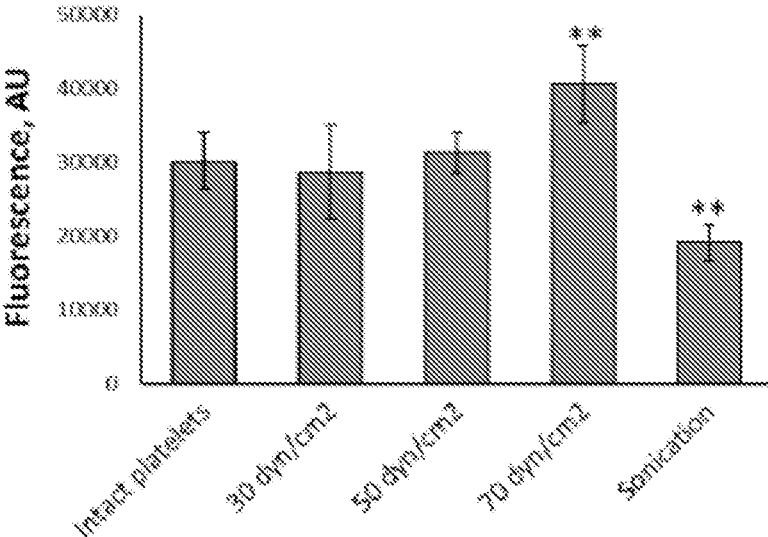

In contrast, platelets subjected to shear stress have shown prominent annexin V binding capacity indicating the appearance of phosphatidylserine on membrane surface. As shown in FIGS. 8A-8F, the fluorescence intensity and the number of annexin V-positive platelets were evidently increased after SMPA, the extent of annexin V binding increase in parallel with the shear force magnitude. Sonication, being a positive control for mechanical activation, alike resulted in dramatic augmentation of annexin V binding, approximately 50% of cells were found to expose phosphatidylserine on their surface (FIG. 8E). It's noteworthy that significant intensification of annexin V binding was observed even after platelet activation by relatively low shear conditions, e.g., 30 dynes/cm$^2$ (FIG. 8B). The last observation denotes high sensitivity of platelet membrane PSE to mechanical activation. The distribution of fluorescence intensity within shear-treated platelet groups appeared as high narrow peaks (FIGS. 8A-8E), indicating a uniformity of PSE response to shear stress. The MFI tended to increase with the shear magnitude, although the significant change was shown only after platelet exposure to high shear stress (FIG. 8G, "70 dynes/cm2" vs. "Intact platelets", ANOVA p<0.01). Sonication, as positive control for mechanical activation, indeed resulted in dramatic augmentation of annexin V binding, with 45.02±7.52% of cells exposing phosphatidylserine on their surface (FIG. 8F).

Figure 9A:
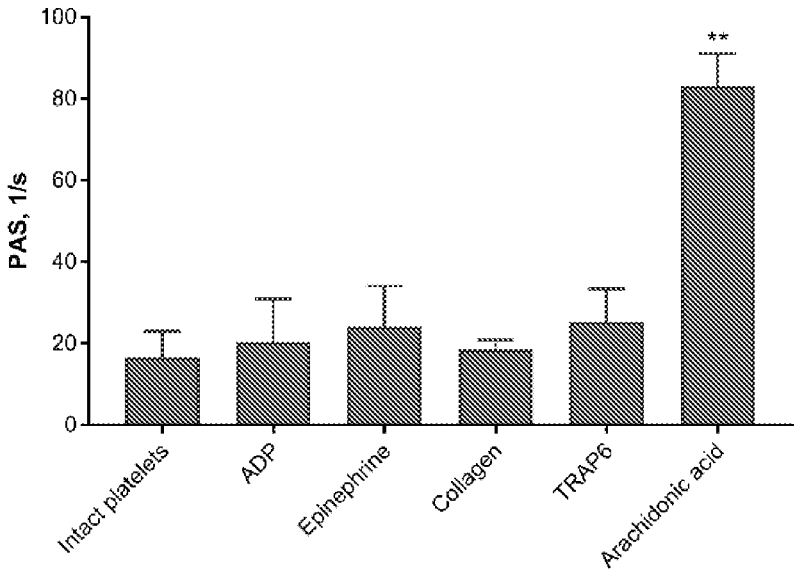
FIGS. 9A-9B are bar graphs showing thrombin generation on the surface of human platelets as measured with pro-thrombinase-based platelet activation state (PAS) assay in intact platelets, or GFP ($20 \times 10^3$ cells/μL) stimulated with biochemical activators including ADP, epinephrine, collagen, TRAP-6, and arachidonic acid along with 2.5 mM CaCl$_2$) undisturbed for 10 min at room temperature (FIG. 9A); or in GFP ($20 \times 10^3$ cells/μL) sheared utilizing HSD constant modes 30, 50, or 70 dynes/cm$^2$ for 10 min at room temperature, and in the positive control treated with sonication (FIG. 9B). The bar graphs represent 4 independent experiments with different donors, mean value±margins of error as error bars are plotted. P values were calculated vs intact platelets by one-way ANOVA: *-p≤0.05, **-p≤0.01; for bars without asterisks, p>0.05.

The chromogenic PAS assay was applied to quantify the amount of thrombin generated on activated platelet surface presenting negatively charged phospholipids, and thus to measure the procoagulant activity of platelets activated with biochemical agonists or shear stress. Platelets stimulated with biochemical mediators did not catalyzed prothrombin activation by factor Xa and hence thrombin generation on platelet surface. Specifically, no amidolytic activity was detected in presence of platelets stimulated by ADP, epinephrine, collagen, or TRAP-6 (FIG. 9A). The potency of arachidonic acid-treated platelets to force thrombin formation was comparable with sonicated GFP sample, established as positive control for SMPA.

Figure 9B:
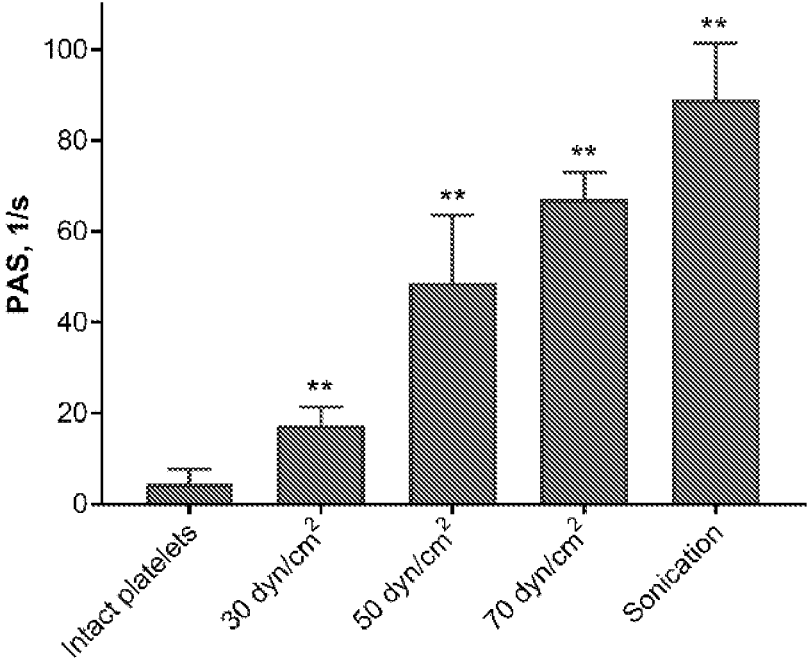

Similar to the observation based on flow cytometry results indicating PSE after SMPA, platelets subjected to shear stress have expressed notable procoagulant activity (FIG. 9B). The rate of the enzymatic reaction of prothrombin activation strongly correlated with applied shear stress magnitude and reached 70.0±1.2% of sonication value when platelet stimulated by 70 dyn/cm² shear stress conditions (FIG. 9B). Platelets exposed to physiologically relevant shear stress levels (30 and 50 dyn/cm²) indeed expressed notable procoagulant activity.

Figure 10A:
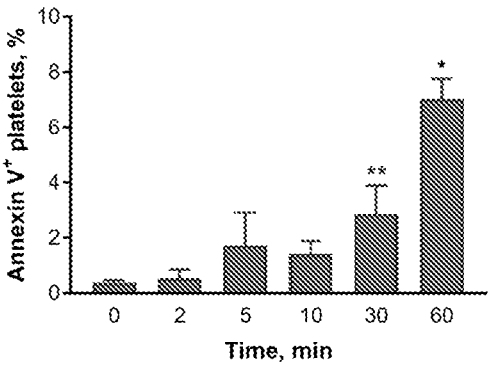
FIGS. 10A-10C are bar graphs showing phosphatidylserine externalization (FIG. 10A), procoagulant activity (FIG. 10B), P-selectin exposure (FIG. 10C), and of platelets recirculated through the VAD-employed loop system. GFP ($20 \times 10^3$ cells/μL) were recirculated through Heart Assist V-utilizing model circulatory system for 1 hour at room temperature, timing GFP samples were collected and processed immediately. On bar graphs data of 4 (6 for C) independent experiments with different donors are summarized, mean value+margins of error as error bars are plotted. P values were calculated vs intact platelets by one-way ANOVA: *-p≤0.05, **-p≤0.01; for bars without asterisks, p>0.05.
Figure 10B:
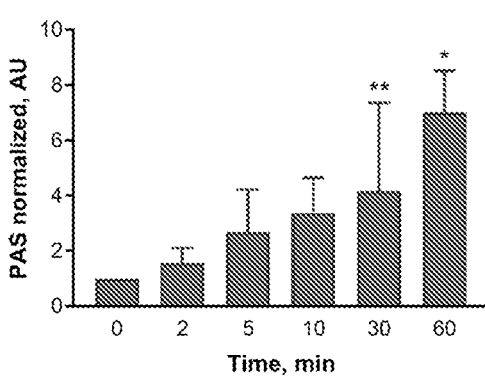
Figure 10C:
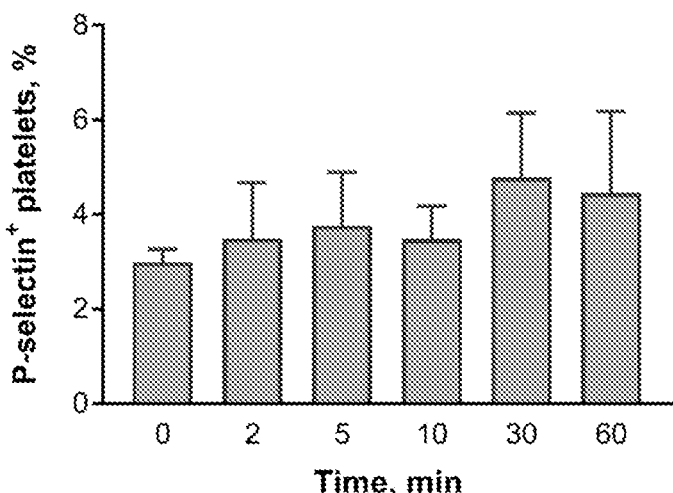

Example 4: Molecular "Signature" of SMPA Under
VAD-Generated Dynamic Shear Stress within the
Heart Assist V-Utilizing Model Circulatory System Results To compare platelet function alterations underlying SMPA by uniform constant shear stress applied in the HSD with actual dynamic shear conditions of VAD-supported circulation, GFP was recirculated through the VAD-utilizing loop system. Platelet P-selectin exposure, as representative marker of platelet biochemical activation, versus PSE and platelet prothrombinase activity, found to depict early stages of mechanical activation, were simultaneously evaluated. It was observed that platelets experienced long-term dynamic shear stress in VAD loop system showed exponential augmentation of annexin V binding over exposure time (FIG. 10A). After 30 and 60 min passage, the number of annexin V-positive platelets was significantly elevated and reached 3.3±0.5% and 7.0±0.7% as compared 0.5±0.1% in non-sheared sample, whereas no P-selectin exposure has been detected in those platelet samples (FIG. 10C). Procoagulant activity of VAD loop-sheared platelets was also elevated (FIG. 10B). As it has been shown by PAS assay, the rate of prothrombin activation by factor Xa was approximately 7-fold increased after 60 min shear exposure to dynamic shear pattern of VAD-employed circulatory system as compared with baseline.

This work has defined a molecular marker specific for SMPA as compared with biochemical platelet activation by physiologically relevant soluble agonists. The effect of physiological and sub-pathological shear forces on human platelet activation was investigated utilizing the hemodynamic shearing device (HSD), a cone-plate-Couette viscometer, specifically designed to generate precisely controlled and uniformly distributed shear stress to all platelets in the flow field (Nobili et al., *ASAIO J. (American Soc. Artif. Intern. Organs)*, vol. 54, no. 1, pp. 64-72, (2008)). Applied shear stress levels were chosen considering results of previous numerical studies of VAD hemodynamics vs physiological levels of shear existing within normal circulatory conditions (Nobili et al., *ASAIO J. (American Soc. Artif. Intern. Organs)*, vol. 54, no. 1, pp. 64-72, (2008)). It has been shown that among examined platelet activation markers (surface P-selectin exposure, integrin αIIbβ3 expression and activation) none could reveal ongoing SMPA. Alternatively, the extent of platelet annexin V binding, reflecting anionic phospholipid externalization on platelet surface and routinely applied to detect cell apoptosis, positively correlated with level of shear and was detectable even on initial stages of SMPA when low level of continuous uniform shear was applied. After being identified for uniform continuous shear stress conditions of the HSD, the SMPA signature has been validated under highly dynamic shear environment in the VAD-employing loop system, indicating its value as a diagnostic signature for SMPA under MCS.

Therefore, this study defines specific markers of platelet activation by shear stress as compared with biochemical activation by physiologically relevant agonists. To induce SMPA in vitro, platelets were exposed to either 1) uniform continuous shear in the HSD (physiologically relevant and elevated shear stress levels were tested), or 2) dynamic shear pattern of axial cfVAD-employed loop system. The extent of platelet activation was monitored utilizing both quantitative and functional approaches. Platelet activation markers (P-selectin exposure and integrin αIIbβ3 activation) as well as annexin V binding reflecting PSE on platelet surface were evaluated by flow cytometry. Additionally, platelet procoagulant activity was assessed by chromogenic prothrombinase-based PAS assay measuring thrombin generation on platelet surface after their stimulation. It was found that continuous shear stress (but not biochemical agonists) induced prominent PSE and hence promoted thrombin generation on the platelet surface. Both the extent of annexin V binding and the rate of thrombin generation strongly correlated with the magnitude of shear stress to which platelets were subjected. Simultaneously, neither P-selectin exposure nor integrin αIIbβ3 activation usually accompanying biochemical platelet activation were markedly elevated after SMPA. Moreover, even low levels of continuous shear stress (30 and 50 dyn/cm²), when applied uniformly to all platelets in the flow field of the HSD, resulted in significant increase of both platelet PSE and procoagulant activity. Further observation indicates that platelet membrane lipid bilayer reorganization and procoagulant surface formation occur (and could be detected) on early stages of SMPA when platelets experience moderate shear stress, more likely existing in vivo within highly dynamic flow conditions in VAD-supported circulation. Thus, utilizing VAD-employed loop system, it was verified that platelet long-term exposure to dynamic shear stress indeed induced exponential elevation of PSE and thrombin generation rates (as quantified by PAS assay), while P-selectin exposure remained persistent over time. Both annexin V binding and PAS levels were considerably lower as compared with those detected within platelet activation by continuous shear (though significantly increased versus non-sheared control). Observed similarity of the molecular marker patterns for platelet activation under dynamic and continuous shear stress conditions validates feasibility of PSE as a specific and sensitive indicator of platelet activation by shear stress.

Analyzing the competence of biochemical agonists to induce platelet activation and PSE, it was shown that each of them promotes distinctive pattern of molecular markers appearing on platelet surface after the activation. Although all agonists were potent drivers of platelet aggregation in GFP and/or PRP, their ability to stimulate P-selectin exposure, integrin GPIIb/IIIa activation and PSE varied drastically. This heterogeneity of biochemical activation response reflects the diversity of signaling pathways involved in its implementation. It was found that only ADP and thrombin taken alone were capable to provoke high magnitude P-selectin exposure and GPIIb/IIIa activation. Interestingly, both ADP and thrombin simultaneously activate multiple types of G-protein coupled receptors: ADP operates through purinergic receptors P2Y1 and P2Y12 associated with Gq- and Gi-proteins, when thrombin drives protease activated receptors PAR1 and PAR4 associated with Gq, Gi and G11. Such cooperative interaction between Gq- and Gi-associated receptors' signals is needed to enhance downstream platelet response and to promote long-term activation events, i.e. integrin activation and aggregation which require permanent platelet stimulation (Delaney et al., "Agonist-induced platelet procoagulant activity requires shear and a Rac1-dependent signaling mechanism," vol. 124, no. 12, pp. 1957-1967, (2014), Ramström et al., *Thromb. Haemost.*, vol. 89, no. 1, pp. 132-41, January (2003)). Therefore, TRAP6, specific PAR1 activator, as well as epinephrine, operating ultimately through Gi-associated a2-adrenergic receptors, were failed to induce full extent platelet activation. Stimulation by these agonists resulted in P-selectin exposure, but no GPIIb/IIIa activation has been detected. In the meantime, platelet incubation with combination of sub-activating concentrations of ADP and epinephrine led to notable integrin activation. It is worth highlighting that neither thrombin nor ADP induced platelet PSE under the experimental conditions, which indicates that additional co-stimulatory support from other than G-protein signaling is required to promote platelet membrane phospholipids' scrambling. Taken as agonist of TXA2-operated pathway, arachidonic acid appeared the only biochemical agent simultaneously provoking notable PSE, P-selectin exposure and platelet aggregation. The exclusive ability of arachidonic acid to induce such high extent platelet response could be explained by its heterogenous effect on cell functions. In human platelets arachidonic acid stimulates enormous increase of intracellular calcium concentration, driven by both $Ca^{2+}$ influx through plasmatic membrane and its release from intracellular stores (Alonso, *Biochem. J*, vol. 272, pp. 435-443, 1990)). While $Ca^{2+}$ release could be prevented by cyclooxygenase inhibitors and mimicked by TXA2 receptor agonist, $Ca^{2+}$ influx required higher AA concentration (60 uM) and was not sensitive to those inhibitors. Recently, Rukoyatkina et al. showed that sub-millimolar concentrations of arachidonic acid could also induce the decline in platelet mitochondrial membrane potential, increase in annexin V binding, and cleavage of procaspase 3, similarly to known proapoptotic agent ABT-737 (Ramström et al., *Thromb. Haemost.*, vol. 89, no. 1, pp. 132-41, January (2003)). In several cancer cell lines TNF-alpha-induced elevation of intracellular arachidonic acid level is also associated with the increase of mitochondria permeability, release of cytochrome c, PSE, caspase 3 activation, following chromatin fragmentation and rapid cell death.

In summary, these experimental findings showed that platelet mechanical activation by shear stress, but not by vast majority of biochemical agonists, induce PSE and thrombin generation on platelet surface. Even dynamic shear conditions existing within VAD-supported circulation result in notable increase of annexin V binding. AA taken in submillimolar concentration was the only agonist capable to provoke PSE. It is known that AA-evoked PSE could be associated either with powerful $Ca^{2+}$ signal driven by this fatty acid or with platelet apoptotic response on high concentration of AA. Which scenario of platelet response is implemented under shear stress conditions remains unclear. The incredible potency of low magnitude shear stress to induce fast PSE indicates that signaling pathways other than biochemically evoked are involved or an alternative amplification mechanism of platelet response is employed.

Platelet membrane reorganization and following PSE occur as a result of $Ca^{2+}$ evoked scramblase activity disturbing membrane lipid bilayer asymmetry and delivering aminophospholipids, phosphatidylserine and phosphatidylethanolamine, from inner to outer membrane leaflet. These negatively charged phospholipids serve as high affinity binding sites for coagulation factors, facilitating tenase and prothrombinase complexes assembly and, thereby, catalyze thrombin generation on platelet surface. Platelet PSE is not energy-consumable but indeed requires high and persistent rise of intracellular $Ca^{2+}$ concentration (up to 1 uM), hardly achieved under the platelet stimulation by physiologically relevant biochemical agonists. As it was shown lately (van der Meijden et al, *Thromb. Haemost.*, vol. 93, no. 6, pp. 1128-1136, (2005), Wolfs et al., *C. Cell. Mol. Life Sci*, vol. 6205, pp. 1514-1525, (2005), Delaney et al., "Agonist-induced platelet procoagulant activity requires shear and a Rac1-dependent signaling mechanism," vol. 124, no. 12, pp. 1957-1967, (2014)) and confirmed in the study, platelet stimulation with agonists operating either single (epinephrine, TRAP-6) or multiple (ADP, thrombin) type of G-protein coupled receptors did not result in any detectable annexin V binding, although successfully drove platelet aggregation (under stirring conditions), integrin activation and/or alpha-granule exocytosis. Thus, platelet agonist-stimulated PSE requires simultaneous application of multiple biochemical agents or shear force co-stimulation engaging alternative $Ca^{2+}$-mobilizing pathways.

Unless defined otherwise, all technical and scientific terms used have the same meanings as commonly understood by one of skill in the art to which the disclosed invention belongs. Publications cited and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method comprising
  (i) assaying isolated platelets from a subject at risk of developing a thrombotic disease, state, or condition for levels of
  (b1) thrombin, (a1) phosphatidylserine, (c1) integrin GPIIb/IIIa activation, (e1) P-selectin; and optionally one or more of (d1) glycoprotein GP Ib, (f1) platelet size; (g1) microparticle generation, and (h1) lipidomic profile of the membrane; and
  (ii) determining the isolated platelets contain one or more platelets activated by one or more mechanical stimuli and the risk of developing a thrombotic disease, state, or condition is related thereto when
    (b2) thrombin level on the external surface of the platelets is elevated relative to the thrombin level of the control;
    (a2) phosphatidylserine level on the external surface of the platelets is elevated relative to the phosphatidylserine level of a control;
    (c2) integrin GPIIb/IIIa activation level on the external surface of the platelets is not increased by more than 20% compared to the integrin GPIIb/IIIa activation level of the control; and
    (e2) P-selectin level on the external surface of the platelets is not increased by more than 20% compared to the P-selectin level of the control; and optionally one or more of (d2) glycoprotein GP Ib level on the external surface of the platelets is about the same or less compared to the glycoprotein GP Ib level of the control;

(f2) platelet size is decreased relative to the platelet size of the control;

(g2) microparticle generation is increased relative to the microparticle generation of the control, and (h2) membrane lipidomic profile is changed compared to the membrane lipidomic profile of the control; and (iii) treating the subject to prevent, reduce, or manage the onset or development of mechanical stimuli-associated thrombosis.

2. The method of claim 1, wherein the mechanical stimuli is selected from shear, vibration, audible sound, ultrasound, acoustic stimulation, pressure, and combinations thereof.

3. The method of claim 1, wherein the platelets are isolated from a blood sample of a subject.

4. The method of claim 2, wherein the mechanical stimuli is shear and further comprising reducing shear-activated platelets in the blood of the subject comprising administering to the subject a pharmaceutical composition comprising one or more mechanoceuticals in an amount effective to reduce the level of phosphatidylserine, the level of thrombin, and/or the level of microparticle generation; to increase in platelet size; or to change membrane lipidomic profile; or a combination thereof; optionally without affecting the level of integrin GPIIb/IIIa activation, the level of integrin GP Ib, and/or the level of P-selectin in the platelets of the subject.

5. The method of claim 4, further comprising monitoring the treatment of a subject comprising:

assaying levels of (b1), (a1), (c1), and (e1) in blood samples collected from a subject before and after treatment respectively, one or more times with mechanoceutical, and repeating treatment if the level of phosphatidylserine, the level of thrombin, the level of microparticle generation is reduced; the platelet size is increased; and/or the membrane lipidomic profile is changed; optionally the level of integrin GPIIb/IIIa activation, the level of integrin GP Ib, and/or level of P-selectin in the platelets of the subject is not affected.

6. The method of claim 5, wherein if the level of phosphatidylserine, the level of thrombin, the level of microparticle generation is not reduced; the platelet size is not increased; and/or the membrane lipidomic profile is not changed;

increasing the dose, the frequency of administration of the mechanoceutical, or a combination thereof, or administering to the subject a different mechanoceutical.

7. The method of claim 6, further comprising one or more additional cycles of assaying levels of (b1), (a1), (c1), and (e1) and treating the subject.

8. The method of claim 1, wherein the subject has a blood-contacting medical device implanted in the body prior to assaying levels of (b1), (a1), (c1), and (e1).

9. The method of claim 8, further comprising implanting a blood-contacting medical device into the subject simultaneously or subsequently to assaying levels of (b1), (a1), (c1), and (e1).

10. The method of claim 1, wherein the control is a population of resting platelets.

11. The method of claim 1, wherein the subject is a human.

12. The method of claim 1, wherein the subject is one with a blood-contacting device optionally selected from mechanical circulatory support devices and ventricular assist devices (VADs).

13. The method of claim 1, wherein the control is platelets from healthy subjects with minimal risk of developing thrombosis.

14. The method of claim 4, wherein the mechanoceutical is a lipid or lipid-related compound, dimethysulfoxide (DMSO), a ganglioside, a hormone, a sterol, cholesterol hemisuccinate, lidocaine, a procaine, a sex steroid, phenytoin, docohexanoic acid, cortisol, estradiol, PGE2, progesterone, medroxyprogesterone, insulin, glucagon, atropine, carbachol, lutropin, neuropeptide Y, thyroid hormone, aldosterone, vasopressin, perylene, 9-(di-cyanovinyl) julodinine, 1,6-diphenyl-1,3,5-hexatiene (DPH), TMA-DPH, DPH-PA, cis or trans-parinaric acid, a polyunsaturated fatty acid, phospatidyl choline, phospahtidylserine, phospatidyl inositol, insitol, choline, cerebroside, a glycoshpingolipid, sphingomyelin, or a combinations thereof.

15. The method of claim 1 further comprising one or more of the measurements of (d1), and (f1)-(h1) the corresponding result(s) in (d2), and (f2)-(h2).

16. The method of claim 1 comprising further comprising two or more of the measurements of (d1), and (f1)-(h1) the corresponding result(s) in (d2), and (f2)-(h2).

17. The method of claim 1 comprising further comprising all four of the measurements of (d1), and (f1)-(h1) the corresponding result(s) in (d2), and (f2)-(h2).

18. The method of claim 1, comprising treating the subject to prevent, reduce, or manage non-mechanical stimuli-associated thrombosis when the subject is not determined to be at risk of developing a thrombogenic disease, state, or condition caused by mechanical stimuli.

19. The method of claim 18, wherein the non-mechanical stimuli comprises chemical or biochemical platelet activation.

20. The method of claim 1, further comprising (iv) determining the isolated platelets contain one or more platelets activated by one or more non-mechanical stimuli-associated and the risk of developing a thrombotic disease, state, or condition is related thereto when (b3) thrombin level on the external surface of the platelets is not elevated relative to the thrombin level of the control;

(a3) phosphatidylserine level on the external surface of the platelets is not elevated relative to the phosphatidylserine level of a control; and optionally (c3) integrin GPIIb/IIIa activation level on the external surface of the platelets is increased compared to the integrin GPIIb/IIIa activation level of the control; and (e3) P-selectin level on the external surface of the platelets is increased compared to the P-selectin level of the control; and optionally one or more of (d3) glycoprotein GP Ib level on the external surface of the platelets is about the same or more compared to the glycoprotein GP Ib level of the control;

(f3) platelet size is not decreased relative to the platelet size of the control;

(g3) microparticle generation is not increased relative to the microparticle generation of the control, and (h2) membrane lipidomic profile is changed compared to the membrane lipidomic profile of the control;

(v) treating the subject to prevent, reduce, or manage the onset or development of non-mechanical stimuli-associated thrombosis.

* * * * *